United States Patent
Lu et al.

(10) Patent No.: US 10,413,904 B2
(45) Date of Patent: Sep. 17, 2019

(54) PACKAGING FOR MULTIPLEXED ASSAYS

(71) Applicant: MESO SCALE TECHNOLOGIES, LLC, Rockville, MD (US)

(72) Inventors: Yihong Claire Lu, Gaithersburg, MD (US); Pankaj Oberoi, Rockville, MD (US)

(73) Assignee: Meso Scale Technologies, Rockville, MD (US)

( * ) Notice: Subject to any disclaimer, the term of this patent is extended or adjusted under 35 U.S.C. 154(b) by 226 days.

(21) Appl. No.: 14/847,381

(22) Filed: Sep. 8, 2015

(65) Prior Publication Data
US 2016/0067707 A1  Mar. 10, 2016

Related U.S. Application Data

(60) Provisional application No. 62/047,144, filed on Sep. 8, 2014.

(51) Int. Cl.
| | |
|---|---|
| *B01L 3/00* | (2006.01) |
| *C12Q 1/6876* | (2018.01) |
| *G01N 33/543* | (2006.01) |
| *C12Q 1/6804* | (2018.01) |
| *G01N 33/68* | (2006.01) |
| *C12Q 1/6816* | (2018.01) |

(52) U.S. Cl.
CPC ........ *B01L 3/50853* (2013.01); *C12Q 1/6804* (2013.01); *C12Q 1/6816* (2013.01); *C12Q 1/6876* (2013.01); *G01N 33/54306* (2013.01); *G01N 33/54353* (2013.01); *G01N 33/6845* (2013.01); *B01L 2300/021* (2013.01); *B01L 2300/043* (2013.01); *B01L 2300/0609* (2013.01); *B01L 2300/0829* (2013.01); *G01N 2458/10* (2013.01)

(58) Field of Classification Search
CPC .......... B01L 3/50853; G01N 33/54306; G01N 33/54353; G01N 33/6854; C12Q 1/6804; C12Q 1/6816; C12Q 1/6876
USPC ......................................................... 422/430
See application file for complete search history.

(56) References Cited

U.S. PATENT DOCUMENTS

| | | | | |
|---|---|---|---|---|
| 5,722,553 | A * | 3/1998 | Hovatter | B01L 3/5085 220/23.8 |
| 6,601,725 | B2 * | 8/2003 | Lafond | B01L 3/50853 220/23.4 |
| 2009/0129978 | A1 * | 5/2009 | Wilson | C12Q 1/6813 422/400 |
| 2014/0112845 | A1 * | 4/2014 | Edens | B01L 3/50853 422/569 |
| 2014/0206412 | A1 * | 7/2014 | DeJohn | B01L 7/52 455/556.1 |

FOREIGN PATENT DOCUMENTS

WO  WO 2014/143044  * 9/2014

* cited by examiner

*Primary Examiner* — Jill A Warden
*Assistant Examiner* — Jacqueline Brazin
(74) *Attorney, Agent, or Firm* — Scully, Scott, Murphy & Presser, P.C.

(57) ABSTRACT

The invention relates to kits and components thereof used in the conduct of solid-phase binding assays.

33 Claims, 9 Drawing Sheets
Specification includes a Sequence Listing.

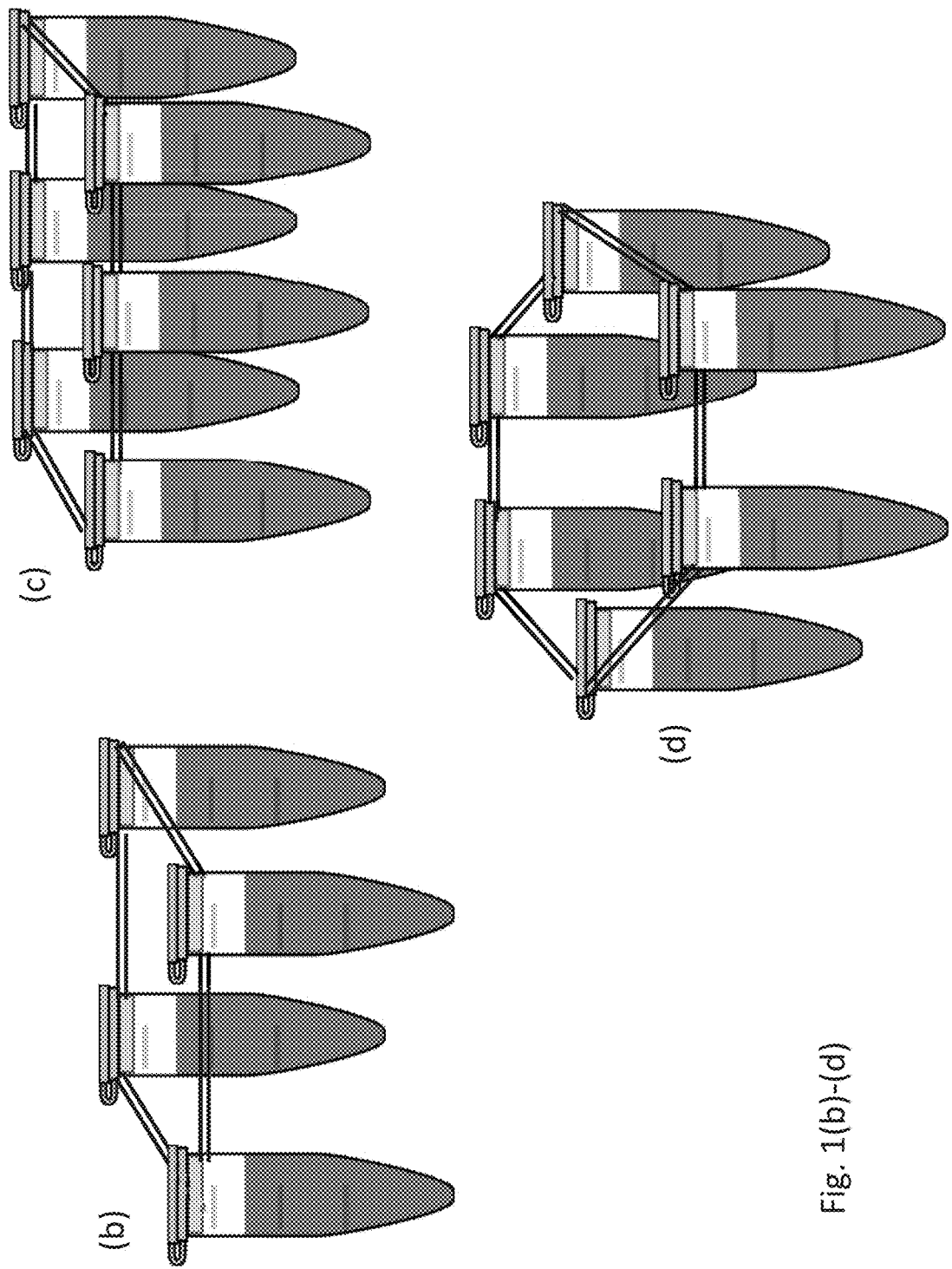
Fig. 1(b)-(d)

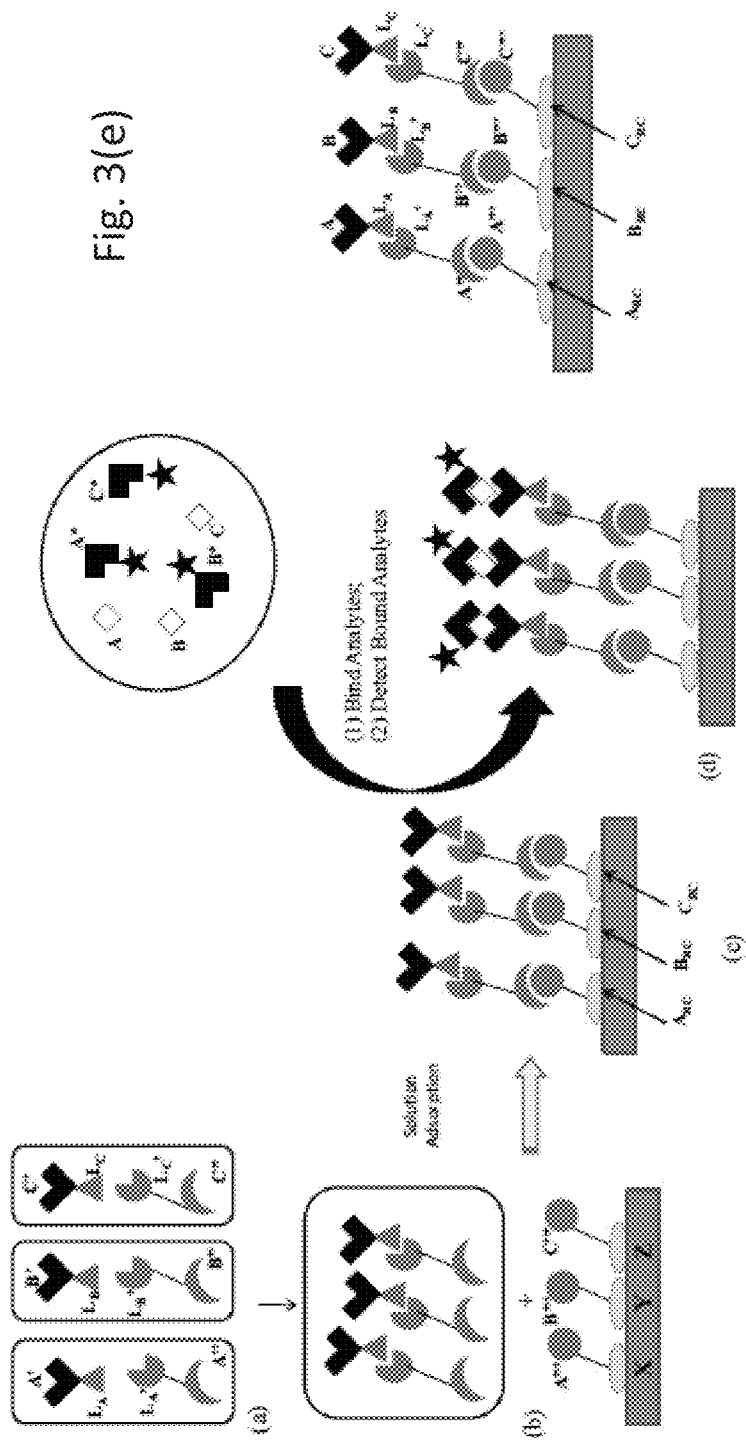

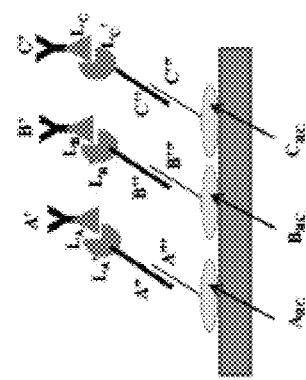
Fig. 4(e)
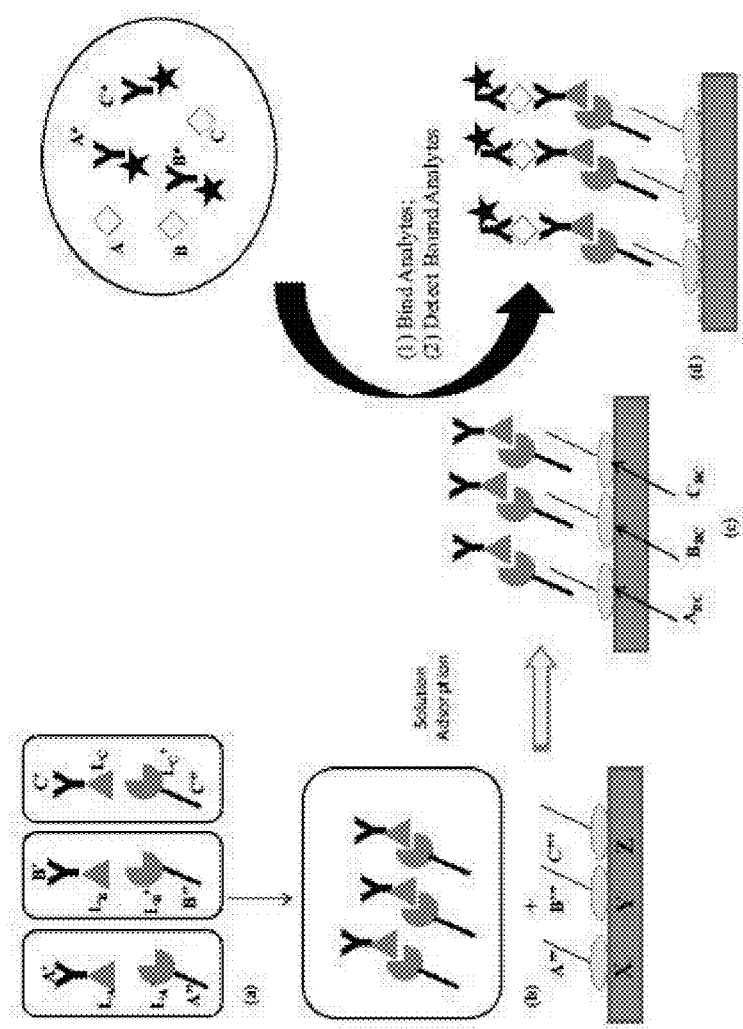
Fig. 4(a)-(d)

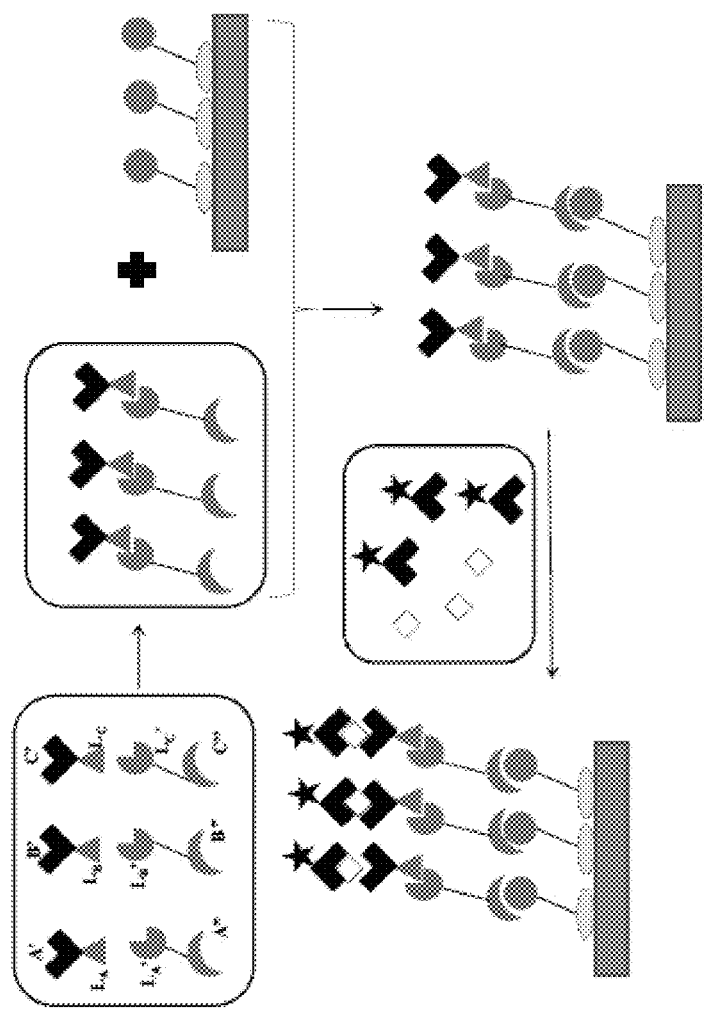
Fig. 5(b) – modify fig

SEQUENCE LISTING

<160> NUMBER OF SEQ ID NOS: 50

<210> SEQ ID NO 1
<211> LENGTH: 12
<212> TYPE: DNA
<213> ORGANISM: Artificial Sequence
<220> FEATURE:
<223> OTHER INFORMATION: oligonucleotide

<400> SEQUENCE: 1
acatcggtag tt                                                    12

<210> SEQ ID NO 2
<211> LENGTH: 12
<212> TYPE: DNA
<213> ORGANISM: Artificial Sequence
<220> FEATURE:
<223> OTHER INFORMATION: oligonucleotide

<400> SEQUENCE: 2
aactaccgat gt                                                    12

<210> SEQ ID NO 3
<211> LENGTH: 12
<212> TYPE: DNA
<213> ORGANISM: Artificial Sequence
<220> FEATURE:
<223> OTHER INFORMATION: oligonucleotide

```
<400> SEQUENCE: 3
acgtcccagt tg                                                          12

<210> SEQ ID NO 4
<211> LENGTH: 12
<212> TYPE: DNA
<213> ORGANISM: Artificial Sequence
<220> FEATURE:
<223> OTHER INFORMATION: oligonucleotide

<400> SEQUENCE: 4
caactgggac gt                                                          12

<210> SEQ ID NO 5
<211> LENGTH: 12
<212> TYPE: DNA
<213> ORGANISM: Artificial Sequence
<220> FEATURE:
<223> OTHER INFORMATION: oligonucleotide

<400> SEQUENCE: 5
agaagaagat cc                                                          12

<210> SEQ ID NO 6
<211> LENGTH: 12
<212> TYPE: DNA
<213> ORGANISM: Artificial Sequence
<220> FEATURE:
<223> OTHER INFORMATION: oligonucleotide

<400> SEQUENCE: 6
ggatcttctt ct                                                          12

<210> SEQ ID NO 7
<211> LENGTH: 12
<212> TYPE: DNA
<213> ORGANISM: Artificial Sequence
<220> FEATURE:
<223> OTHER INFORMATION: oligonucleotide

<400> SEQUENCE: 7
aggttcagtg ca                                                          12

<210> SEQ ID NO 8
<211> LENGTH: 12
<212> TYPE: DNA
<213> ORGANISM: Artificial Sequence
<220> FEATURE:
<223> OTHER INFORMATION: oligonucleotide

<400> SEQUENCE: 8
tgcactgaac ct                                                          12

<210> SEQ ID NO 9
<211> LENGTH: 12
<212> TYPE: DNA
<213> ORGANISM: Artificial Sequence
<220> FEATURE:
<223> OTHER INFORMATION: oligonucleotide

<400> SEQUENCE: 9
atcaggatac gc                                                          12

<210> SEQ ID NO 10
<211> LENGTH: 12
```

-continued

```
<212> TYPE: DNA
<213> ORGANISM: Artificial Sequence
<220> FEATURE:
<223> OTHER INFORMATION: oligonucleotide

<400> SEQUENCE: 10
gcgtatcctg at                                                              12

<210> SEQ ID NO 11
<211> LENGTH: 12
<212> TYPE: DNA
<213> ORGANISM: Artificial Sequence
<220> FEATURE:
<223> OTHER INFORMATION: oligonucleotide

<400> SEQUENCE: 11
atcattacca cc                                                              12

<210> SEQ ID NO 12
<211> LENGTH: 12
<212> TYPE: DNA
<213> ORGANISM: Artificial Sequence
<220> FEATURE:
<223> OTHER INFORMATION: oligonucleotide

<400> SEQUENCE: 12
ggtggtaatg at                                                              12

<210> SEQ ID NO 13
<211> LENGTH: 12
<212> TYPE: DNA
<213> ORGANISM: Artificial Sequence
<220> FEATURE:
<223> OTHER INFORMATION: oligonucleotide

<400> SEQUENCE: 13
attaacggga gc                                                              12

<210> SEQ ID NO 14
<211> LENGTH: 12
<212> TYPE: DNA
<213> ORGANISM: Artificial Sequence
<220> FEATURE:
<223> OTHER INFORMATION: oligonucleotide

<400> SEQUENCE: 14
gctcccgtta at                                                              12

<210> SEQ ID NO 15
<211> LENGTH: 12
<212> TYPE: DNA
<213> ORGANISM: Artificial Sequence
<220> FEATURE:
<223> OTHER INFORMATION: oligonucleotide

<400> SEQUENCE: 15
cagaggtctt aa                                                              12

<210> SEQ ID NO 16
<211> LENGTH: 12
<212> TYPE: DNA
<213> ORGANISM: Artificial Sequence
<220> FEATURE:
<223> OTHER INFORMATION: oligonucleotide

<400> SEQUENCE: 16
```
ttaagacctc tg                                                      12

<210> SEQ ID NO 17
<211> LENGTH: 12
<212> TYPE: DNA
<213> ORGANISM: Artificial Sequence
<220> FEATURE:
<223> OTHER INFORMATION: oligonucleotide

<400> SEQUENCE: 17
caggtgtcca tt                                                      12

<210> SEQ ID NO 18
<211> LENGTH: 12
<212> TYPE: DNA
<213> ORGANISM: Artificial Sequence
<220> FEATURE:
<223> OTHER INFORMATION: oligonucleotide

<400> SEQUENCE: 18
aatggacacc tg                                                      12

<210> SEQ ID NO 19
<211> LENGTH: 12
<212> TYPE: DNA
<213> ORGANISM: Artificial Sequence
<220> FEATURE:
<223> OTHER INFORMATION: oligonucleotide

<400> SEQUENCE: 19
catccaatcc ag                                                      12

<210> SEQ ID NO 20
<211> LENGTH: 12
<212> TYPE: DNA
<213> ORGANISM: Artificial Sequence
<220> FEATURE:
<223> OTHER INFORMATION: oligonucleotide

<400> SEQUENCE: 20
ctggattgga tg                                                      12

<210> SEQ ID NO 21
<211> LENGTH: 12
<212> TYPE: DNA
<213> ORGANISM: Artificial Sequence
<220> FEATURE:
<223> OTHER INFORMATION: oligonucleotide

<400> SEQUENCE: 21
cctacgatat ac                                                      12

<210> SEQ ID NO 22
<211> LENGTH: 12
<212> TYPE: DNA
<213> ORGANISM: Artificial Sequence
<220> FEATURE:
<223> OTHER INFORMATION: oligonucleotide

<400> SEQUENCE: 22
gtatatcgta gg                                                      12

<210> SEQ ID NO 23
<211> LENGTH: 12
<212> TYPE: DNA
<213> ORGANISM: Artificial Sequence

```
<220> FEATURE:
<223> OTHER INFORMATION: oligonucleotide

<400> SEQUENCE: 23
cgaatgtaga gt                                                         12

<210> SEQ ID NO 24
<211> LENGTH: 12
<212> TYPE: DNA
<213> ORGANISM: Artificial Sequence
<220> FEATURE:
<223> OTHER INFORMATION: oligonucleotide

<400> SEQUENCE: 24
actctacatt cg                                                         12

<210> SEQ ID NO 25
<211> LENGTH: 12
<212> TYPE: DNA
<213> ORGANISM: Artificial Sequence
<220> FEATURE:
<223> OTHER INFORMATION: oligonucleotide

<400> SEQUENCE: 25
cggtttgaga ta                                                         12

<210> SEQ ID NO 26
<211> LENGTH: 12
<212> TYPE: DNA
<213> ORGANISM: Artificial Sequence
<220> FEATURE:
<223> OTHER INFORMATION: oligonucleotide

<400> SEQUENCE: 26
tatctcaaac cg                                                         12

<210> SEQ ID NO 27
<211> LENGTH: 12
<212> TYPE: DNA
<213> ORGANISM: Artificial Sequence
<220> FEATURE:
<223> OTHER INFORMATION: oligonucleotide

<400> SEQUENCE: 27
cttacaacgc ca                                                         12

<210> SEQ ID NO 28
<211> LENGTH: 12
<212> TYPE: DNA
<213> ORGANISM: Artificial Sequence
<220> FEATURE:
<223> OTHER INFORMATION: oligonucleotide

<400> SEQUENCE: 28
tggcgttgta ag                                                         12

<210> SEQ ID NO 29
<211> LENGTH: 12
<212> TYPE: DNA
<213> ORGANISM: Artificial Sequence
<220> FEATURE:
<223> OTHER INFORMATION: oligonucleotide

<400> SEQUENCE: 29
ctttctcggc ac                                                         12
```

```
<210> SEQ ID NO 30
<211> LENGTH: 12
<212> TYPE: DNA
<213> ORGANISM: Artificial Sequence
<220> FEATURE:
<223> OTHER INFORMATION: oligonucleotide

<400> SEQUENCE: 30
gtgccgagaa ag                                                              12

<210> SEQ ID NO 31
<211> LENGTH: 12
<212> TYPE: DNA
<213> ORGANISM: Artificial Sequence
<220> FEATURE:
<223> OTHER INFORMATION: oligonucleotide

<400> SEQUENCE: 31
gacataaagc ga                                                              12

<210> SEQ ID NO 32
<211> LENGTH: 12
<212> TYPE: DNA
<213> ORGANISM: Artificial Sequence
<220> FEATURE:
<223> OTHER INFORMATION: oligonucleotide

<400> SEQUENCE: 32
tcgctttatg tc                                                              12

<210> SEQ ID NO 33
<211> LENGTH: 12
<212> TYPE: DNA
<213> ORGANISM: Artificial Sequence
<220> FEATURE:
<223> OTHER INFORMATION: oligonucleotide

<400> SEQUENCE: 33
gccatagtct ct                                                              12

<210> SEQ ID NO 34
<211> LENGTH: 12
<212> TYPE: DNA
<213> ORGANISM: Artificial Sequence
<220> FEATURE:
<223> OTHER INFORMATION: oligonucleotide

<400> SEQUENCE: 34
agagactatg gc                                                              12

<210> SEQ ID NO 35
<211> LENGTH: 12
<212> TYPE: DNA
<213> ORGANISM: Artificial Sequence
<220> FEATURE:
<223> OTHER INFORMATION: oligonucleotide

<400> SEQUENCE: 35
gctaattcac ca                                                              12

<210> SEQ ID NO 36
<211> LENGTH: 12
<212> TYPE: DNA
<213> ORGANISM: Artificial Sequence
<220> FEATURE:
<223> OTHER INFORMATION: oligonucleotide
```

```
<400> SEQUENCE: 36
tggtgaatta gc                                                          12

<210> SEQ ID NO 37
<211> LENGTH: 12
<212> TYPE: DNA
<213> ORGANISM: Artificial Sequence
<220> FEATURE:
<223> OTHER INFORMATION: oligonucleotide

<400> SEQUENCE: 37
ggtcgtgttt ca                                                          12

<210> SEQ ID NO 38
<211> LENGTH: 12
<212> TYPE: DNA
<213> ORGANISM: Artificial Sequence
<220> FEATURE:
<223> OTHER INFORMATION: oligonucleotide

<400> SEQUENCE: 38
tgaaacacga cc                                                          12

<210> SEQ ID NO 39
<211> LENGTH: 12
<212> TYPE: DNA
<213> ORGANISM: Artificial Sequence
<220> FEATURE:
<223> OTHER INFORMATION: oligonucleotide

<400> SEQUENCE: 39
gttgattctg tc                                                          12

<210> SEQ ID NO 40
<211> LENGTH: 12
<212> TYPE: DNA
<213> ORGANISM: Artificial Sequence
<220> FEATURE:
<223> OTHER INFORMATION: oligonucleotide

<400> SEQUENCE: 40
gacagaatca ac                                                          12

<210> SEQ ID NO 41
<211> LENGTH: 12
<212> TYPE: DNA
<213> ORGANISM: Artificial Sequence
<220> FEATURE:
<223> OTHER INFORMATION: oligonucleotide

<400> SEQUENCE: 41
tacccggaat aa                                                          12

<210> SEQ ID NO 42
<211> LENGTH: 12
<212> TYPE: DNA
<213> ORGANISM: Artificial Sequence
<220> FEATURE:
<223> OTHER INFORMATION: oligonucleotide

<400> SEQUENCE: 42
ttattccggg ta                                                          12

<210> SEQ ID NO 43
```

```
<211> LENGTH: 12
<212> TYPE: DNA
<213> ORGANISM: Artificial Sequence
<220> FEATURE:
<223> OTHER INFORMATION: oligonucleotide

<400> SEQUENCE: 43
tgcttgactt gg                                                          12

<210> SEQ ID NO 44
<211> LENGTH: 12
<212> TYPE: DNA
<213> ORGANISM: Artificial Sequence
<220> FEATURE:
<223> OTHER INFORMATION: oligonucleotide

<400> SEQUENCE: 44
ccaagtcaag ca                                                          12

<210> SEQ ID NO 45
<211> LENGTH: 12
<212> TYPE: DNA
<213> ORGANISM: Artificial Sequence
<220> FEATURE:
<223> OTHER INFORMATION: oligonucleotide

<400> SEQUENCE: 45
ttccacttag gg                                                          12

<210> SEQ ID NO 46
<211> LENGTH: 12
<212> TYPE: DNA
<213> ORGANISM: Artificial Sequence
<220> FEATURE:
<223> OTHER INFORMATION: oligonucleotide

<400> SEQUENCE: 46
ccctaagtgg aa                                                          12

<210> SEQ ID NO 47
<211> LENGTH: 12
<212> TYPE: DNA
<213> ORGANISM: Artificial Sequence
<220> FEATURE:
<223> OTHER INFORMATION: oligonucleotide

<400> SEQUENCE: 47
ttgtctagcg gc                                                          12

<210> SEQ ID NO 48
<211> LENGTH: 12
<212> TYPE: DNA
<213> ORGANISM: Artificial Sequence
<220> FEATURE:
<223> OTHER INFORMATION: oligonucleotide

<400> SEQUENCE: 48
gccgctagac aa                                                          12

<210> SEQ ID NO 49
<211> LENGTH: 12
<212> TYPE: DNA
<213> ORGANISM: Artificial Sequence
<220> FEATURE:
<223> OTHER INFORMATION: oligonucleotide

<400> SEQUENCE: 49
```

```
tttcccttgc ta                                                                 12

<210> SEQ ID NO 50
<211> LENGTH: 12
<212> TYPE: DNA
<213> ORGANISM: Artificial Sequence
<220> FEATURE:
<223> OTHER INFORMATION: oligonucleotide

<400> SEQUENCE: 50
tagcaaggga aa                                                                 12
```

US 10,413,904 B2

PACKAGING FOR MULTIPLEXED ASSAYS

CROSS REFERENCE TO RELATED APPLICATIONS

The present application claims benefit of U.S. Provisional Application No. 62/047,144, filed Sep. 8, 2014, the entire contents of which are incorporated herein by reference. Reference is made to U.S. Provisional Application Ser. Nos. 61/775,860 and 61/778,727, filed Mar. 11, 2013 and Mar. 13, 2013, respectively, the disclosures of each are incorporated herein by reference in its entirety. Reference is also made to the following U.S. application Ser. Nos. 62/013,823, 61/993,581; 14/206,284; 14/208,040, and 14/203,638, the disclosures of which are hereby incorporated herein by reference.

INCORPORATION BY REFERENCE OF SEQUENCE LISTING

The Sequence Listing in the ASCII text file, named as 31385_SequenceListing.txt of 9.38 KB, created on Sep. 8, 2015, and submitted to the United States Patent and Trademark Office via EFS-Web, is incorporated herein by reference.

FIELD OF THE INVENTION

Improved products and packaging for conducting binding assays are provided. These products include an integral assembly for a plurality of spaced containers used in the conduct of a binding assay in a receptacle holder configured to receive the integral assembly, wherein the containers include visual indicators to distinguish the contents of a container from other containers in the assembly. The product also includes an information display element that directs the user through the assay set-up and optionally, assay processing. The products and packaging greatly enhance a user's experience in conducting complex binding assays.

BACKGROUND OF THE INVENTION

A substantial body of literature has been developed concerning techniques that employ binding reactions, e.g., antigen-antibody reactions, nucleic acid hybridization and receptor-ligand reactions, for the sensitive measurement of analytes of interest in samples. The high degree of specificity in many biochemical binding systems has led to many assay methods and systems of value in a variety of markets including basic research, human and veterinary diagnostics, environmental monitoring and industrial testing. The presence of an analyte of interest may be measured by directly measuring the participation of the analyte in a binding reaction. In some approaches, this participation may be indicated through the measurement of an observable label attached to one or more of the binding materials.

Commercially available assays can involve complex set-up and subsequent assay processing protocols. Therefore, there is a need to provide the user a product or product packaging that facilitates reagent preparation and assay processing for complex binding assays.

SUMMARY OF THE INVENTION

The invention provides a kit comprising
(a) an integral assembly of a plurality of spaced containers arranged in an aligned series, wherein each container includes a visual indicator to distinguish a container in the plurality from an additional container in the plurality; and
(b) a receptacle holder comprising (i) a top surface and a top surface support; (ii) a plurality of receptacles positioned on the top surface and configured to receive the integral assembly of containers; and optionally, (ii) a fluid reservoir.

Also included is an integral assembly of a plurality of spaced containers arranged in an aligned series, wherein each container includes a visual indicator to distinguish a container in the plurality from an additional container in the plurality.

A further embodiment is a receptacle holder comprising (i) a top surface and a top surface support; (ii) a plurality of receptacles positioned on the top surface and configured to receive an integral assembly of containers; and optionally, (ii) a fluid reservoir.

BRIEF DESCRIPTION OF DRAWINGS

The accompanying drawings are provided to illustrate rather than limit the scope of the invention.

FIGS. 1(b)-(e) show alternative embodiments of an integral assembly of a plurality of spaced containers.

FIGS. 3(a)-3(e), 4(a)-4(e), 5(a) and 5(b) illustrate alternative embodiments of assay formats conducted using the kits and components described herein.

DETAILED DESCRIPTION OF THE INVENTION

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The present invention provides an improvement to traditional binding assays by providing the user with a flexible product packaging that facilitates the preparation of reagents and/or sample used in the assay. By providing an assembly that includes a plurality of containers configured for reagent preparation, each with a visual indicator to direct the user to the appropriate placement of that container in a platform used in reagent and assay processing steps, the user is guided through the procedure, reducing user error and expediting the assay protocol. The invention provides an assembly comprising a plurality of spaced, individually visually marked, containers and a receptacle holder configured to receive the assembly. The containers in the assembly are configured to enable reagent preparation and the receptacle holder provides a platform for the assembly that enables the proper use of the assembly and it's components in preparation for an assay.

Figure 1A:
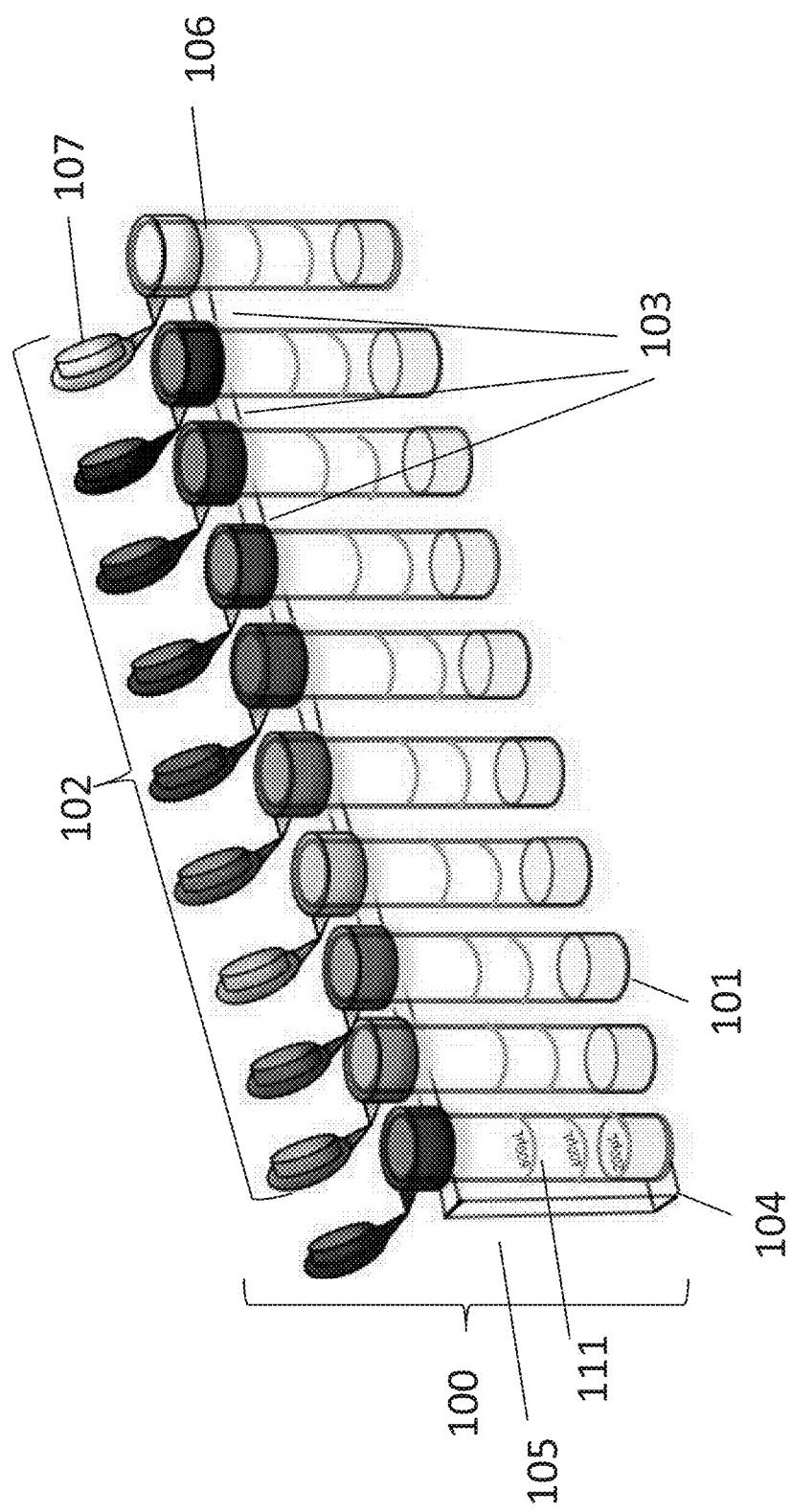
FIG. 1(a) shows one embodiment of an integral assembly of a plurality of spaced containers.

One embodiment of an integral assembly of a plurality of spaced containers is shown in FIG. 1(a). The integral assembly, 100, consists of a multiplicity of containers, 101, in an aligned series, 102, and connected in the assembly by a series of aligned tethers, 103. Preferably, the aligned series comprises a linear elongated uninterrupted strip as shown in FIG. 1(a). Alternatively, as shown in FIG. 1(b)-(d), the invention also contemplates a non-linear series in which the containers are arranged in an array, e.g., a set of containers arranged in a polygonal arrangement including M×M (FIG. 1(b)) or M×N (FIG. 1(c)) aligned containers; or the aligned series can include containers arranged in a circular arrangement (as shown in FIG. 1(d)). The embodiment depicted in FIG. 1(a) includes 10 containers, but the skilled artisan will recognize that the assembly can include any number of containers. For example, the assembly can include up to 25 spaced containers, up to 16 containers, and preferably, up to 10 spaced containers. In another embodiment, the assembly can have fewer than 10 spaced containers, e.g., up to 4 or 7 spaced containers.

Preferably, the integral assembly includes an alignment element, 104, that is configured to mate with and fit within an alignment element receptacle in the receptacle holder in order to ensure that the integral assembly is properly placed in the correct orientation in the receptacle holder. As shown in element 104, the alignment element is a feature of the assembly that is a unique shape or configuration relative to the containers in the plurality. Therefore, in the embodiment shown in FIG. 1(a), the integral assembly comprises a proximate and a distal end (105 and 106, respectively), the plurality of spaced containers are positioned between the proximate and distal ends, and the alignment element is positioned at the proximate end adjacent to the plurality of spaced containers. Another embodiment of the alignment element is to include one or more containers of the plurality with a shape that differs from the remainder of containers in the plurality (not shown). For example, the bottom of the first container can be rectangular instead of round. The alignment element insures that the integral assembly cannot be inserted into the receptacle holder unless it is positioned in the correct orientation.

The containers in the integral assembly can be any suitable vessel for sample or reagent preparation, including and without limitation, vials, ampoules, cups, reaction vessels, test tubes, micro-tubes, or combinations thereof, and the containers can be made of any material suitable for sample or reagent preparation. In a preferred embodiment, the integral assembly is manufactured by injection molding and the assembly and its component parts are made of metal, glass, elastomer, and/or thermoplastic or thermosetting polymers. Alternatively, the containers in the integral assembly can include a media suitable for purification of a reagent or a sample prior to use in an assay. In one embodiment, the containers can be individual spin cups or columns including purification media, e.g., silica or another purification matrix. Still further, purification media can be added to one or more containers in the integral assembly prior to use.

Figure 1E:
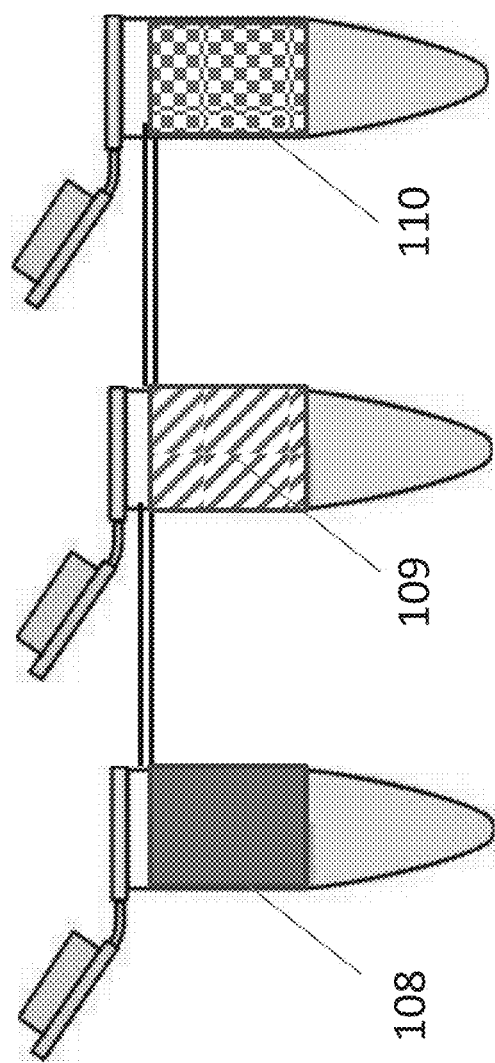

As shown in the embodiment depicted in FIG. 1(a), the containers can include a cap, 107, configured to seal the contents of the container. In addition, as shown in FIG. 1(e), the containers include a visual indicator, 108, 109, and 110, respectively, which differentiates each individual container in the plurality. In the embodiment shown in FIG. 1(a), the visual indicator is on the cap, but any component of the container can include the visual indicator or the entire container can be visually distinct from each additional container in the plurality (e.g., the first container is one color or pattern, whereas the other containers in the assembly are each different colors or patterns). The visual indicator can be a pattern or color, and preferably, the visual indicator is a color. Moreover, as shown in FIG. 1(a), each container can include volumetric markings (111) to indicate the volume of fluid present in the container to visually assist the user in the addition of reagents or sample to the container.

Figure 2A:
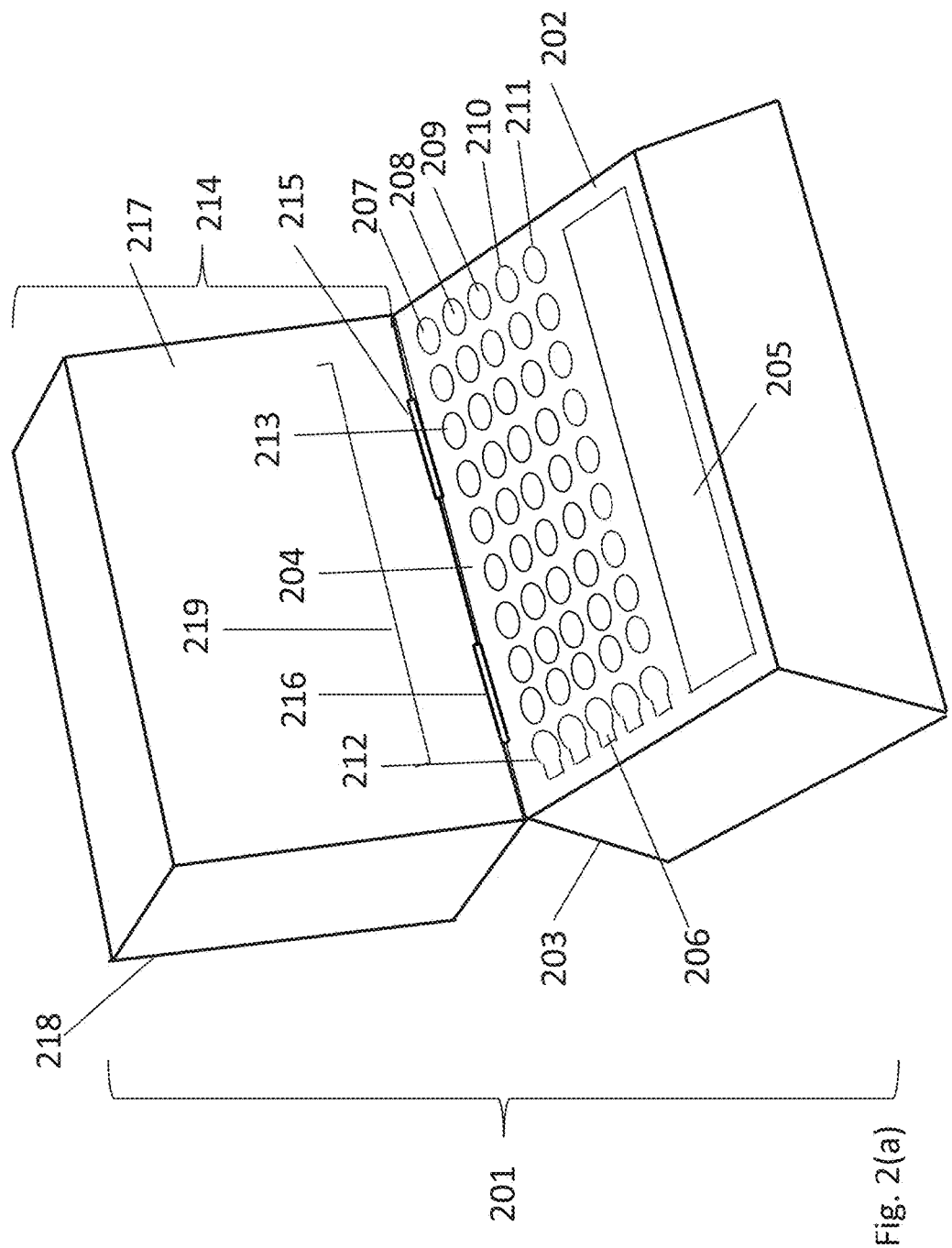
FIG. 2(a) shows the receptacle holder which serves as a platform for the integral assembly and FIG. 2(b) shows an alternative receptacle holder.

The receptacle holder which serves as a platform for the integral assembly is illustrated in FIG. 2(a). The receptacle holder, 201, includes a top surface, 202, a top surface support, 203 (e.g., two or more supporting walls and preferably four supporting walls as shown in FIG. 2(a), a plurality of receptacles, 204, positioned on the top surface and configured to receive the integral assembly of containers; and optionally a fluid reservoir, 205.

Preferably, the plurality of receptacles is arranged in an array. For example, as shown in FIG. 2(a), the array comprises a 5×10 array, but the skilled artisan will recognize that the array can comprise any number or arrangement of receptacles, e.g., a 1×10, 2×10, 3×10, 4×10, 5×10, 6×10, 7×10, 8×10, 9×10, or 10×10 array of receptacles; a 1×4, 2×4, 3×4, 4×4, 5×4, 6×4, 7×4, 8×4, 9×4, or 10×4 array of receptacles; a 1×7, 2×7, 3×7, 4×7, 5×7, 6×7, 7×7, 8×7, 9×7, or 10×7 array of receptacles; a 1×16, 2×16, 3×16, 4×16, 5×16, 6×16, 7×16, 8×16, 9×16, or 10×16 array of receptacles; or a 1×25, 2×25, 3×25 4×25, 5×25, 6×25, 7×25, 8×25, 9×25, or 10×25 array of receptacles. Likewise, the array can be arranged in a linear or non-linear arrangement, e.g., a rectangular, square, or circular pattern to mate with and receive an integral assembly arranged in the same linear or non-linear configuration.

As shown in FIG. 2(a), the array comprises the plurality of receptacles including an alignment element receptacle, 206, configured to receive the alignment element of the integral assembly. The shape of the alignment element receptacle differs from the shape of the other receptacles in the array. Preferably, the array consists of two or more subsets of plural receptacles, wherein each subset includes an alignment element receptacle and the shape of the alignment element receptacle in a subset differs from the shape of the remaining receptacles in the subset. For example, as shown in FIG. 2(a), the 5×10 array comprises five subsets of plural receptacles, 207-211, and the shape of the alignment element receptacle in the first subset, 212, differs from the shape of the remaining receptacles in that subset, e.g., receptacle 213.

In the embodiment shown in FIG. 2(a), the receptacle holder includes a cover, 214, e.g., attached to the top surface, e.g., by one or more hinge elements, 215 and 216. The cover in FIG. 2(a) includes an inner surface, 217, and an outer surface, 218, wherein the inner surface is positioned to face the top surface of the receptacle holder. The cover can also be configured to hold a kit information display element (not shown in FIG. 2(a)), e.g., via an attachment element, 219, affixed to the inner surface to attach the information display element to the inner surface of the cover. The attachment element can be a pin, clip, shelf, or insert in the cover that is configured to receive an information display element, e.g., made of cardstock, plastic, paper, etc. In an alternative embodiment not shown in FIG. 2(a), the kit information display element can be displayed or provided separately from the kit, e.g., as a screen or module in a graphical user interface attached to a device used to conduct an assay.

The kit information display element includes instructions for set-up of the kit, instructions for use of the kit and its components, and/or combinations thereof. In a specific embodiment, the kit information display element is provided with the kit, directly, as a component of the kit packaging, or remotely, e.g., via an online or externally provided resource, and it includes detailed instructions for the addition and/or handling of samples and/or reagents in the integral assembly before, during, and after the addition of the assembly into the receptacle holder. For example, the kit information display element can include step-by-step instructions for sample preparation prior to addition of the sample into one or more containers in the integral assembly, including the addition of reagents to the sample, the quantity and type of reagents required, the order of addition and/or method of addition, and how one or more subsequent steps in sample and/or reagent preparation should be carried out by the user for a given assay protocol. In yet another embodiment, the kit information display element is accessible via a manufacturer's or distributor's website or as an email attachment to an authorized user. To access the kit information display element, the user may input a catalog or other kit identifier that identifies the kit, its contents, and the associated kit protocol, in the manufacturer's or distributor's catalog of products, and the website displays the kit information display element to the user via the website or emails the element as an attachment to an authorized user.

In one embodiment, the kit comprises an identifier comprising non-volatile memory including kit set-up information, kit usage information, or combinations thereof. Non-volatile memory is computer memory that can retain the stored information without power. Examples of non-volatile memory which may be used in the identifier include, but are not limited to, electronic non-volatile memory (e.g., read-only memory and flash memory), magnetic memory (e.g., hard disks, floppy disk drives, and magnetic tape), optical memory (optical disc drives) and hybrids of these approaches (e.g., magneto-optical memory). In one embodiment, the identifier is a bar code; a smart card, chip card, or integrated circuit card (ICC) (referred to collectively as "ICCs"); EEPROM, EPROM, and/or RFID. In a preferred embodiment, the non-volatile memory is an EEPROM, RFID, or bar code, and particularly preferred is a bar code. Preferably, the assay system or reader used with the kit of the present invention includes an identifier controller that reads the non-volatile memory and optionally, controls the operation of the non-volatile memory and other components of the assay system. The identifier controller optionally includes a micro-controller to interface with the non-volatile memory over a communication interface, which may incorporate conventional interface architectures and protocols such as I2C, a two line serial bus protocol. The microcontroller addresses the non-volatile memory and performs write, read and erase operations on the memory. In practice, the identifier controller reads the non-volatile memory associated with the kit (which can be included with the kit packaging) and adjusts the system for use of the kit based on the data stored to the non-volatile memory. In this regard, reference is made to copending U.S. application Ser. Nos. 12/844,345 and 13/191,000, the disclosures of which are incorporated herein by reference.

Therefore, in those embodiments in which the kit includes non-volatile memory, the data included in the kit information display element is stored in the non-volatile memory and when read by the identifier controller, the kit information display element is displayed as a component of the graphical user interface of the device or reader associated with the identifier controller. Alternatively, the kit information display element can be displayed on a computer attached or otherwise associated with the device or reader. "Computer" or "computer system" as used herein shall mean one or more computing devices, regardless of the number and location of processing elements. For example and without limitation, the term computer or computer system includes personal computers, desktop computers, tablet computers, computer networks, personal digital assistants (PDAs), mobile phones (whether smart phones, PDA phones or digital cell phones), portable e-mail devices, media players, and so forth. In addition, a computer system can provide access to two or more users at different computers in the same or different locations, in direct or indirect contact with a server(s) and/or each other via a network.

Figure 2B:
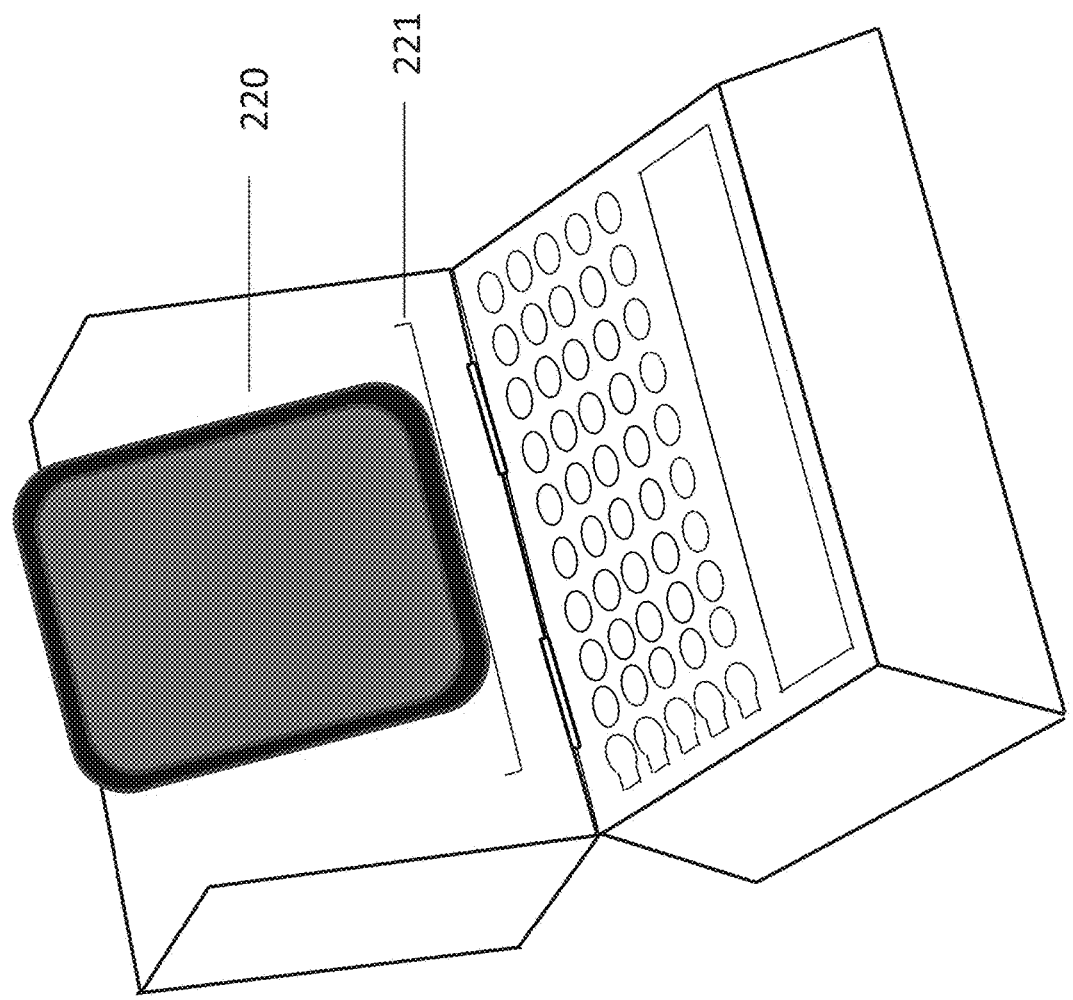

Hence, one specific embodiment of the invention is a kit in which the kit information is displayed as a component of a graphical user interface on computer, e.g., a tablet or mobile phone. The receptacle holder is optionally adapted to include a shelf or platform for a tablet or mobile device, e.g., so that the tablet or mobile device can be supported in front of or adjacent to the receptacle housing to enable the user to view the kit information displayed thereon. One version of this embodiment is shown in FIG. 2(b), with a tablet or mobile device, 220, supported on the receptacle housing by a shelf or platform, 221. In an alternative embodiment, a tablet or mobile device can be support on a separate platform or shelf adjacent to the receptacle housing (not shown).

In the embodiment depicted in FIG. 2(a), the receptacle housing includes a fluid reservoir, 205, however, the fluid reservoir can be provided as an additional component that is not an element of the receptacle housing. In a preferred embodiment, the fluid reservoir incorporated in the receptacle housing is configured to receive a disposable fluid reservoir, e.g., a disposable container, dish, or bowl that can be discarded after one or more uses in the receptacle housing.

The kit can optionally include one or more assay consumables used in the conduct of a binding assay, e.g., one or more multi-well assay plates, cartridges, reaction vessels, coated or uncoated microparticles, test tubes, cuvettes, flow cells, assay chips, lateral flow devices, etc., and/or combinations thereof. In certain embodiments, the kits and components of the present invention may employ assay reagents that are stored in a dry state and the components/kits may further comprise or be supplied with desiccant materials for maintaining the assay reagents in a dry state. Components preloaded with the assay reagents can greatly improve the speed and reduce the complexity of assay measurements while maintaining excellent stability during storage. The dried assay reagents may be any assay reagent that can be dried and then reconstituted prior to use in an assay. These include, but are not limited to, binding reagents useful in binding assays, enzymes, enzyme substrates, indicator dyes and other reactive compounds that may be used to detect an analyte of interest. The assay reagents may also include substances that are not directly involved in the mechanism of detection but play an auxiliary role in an assay including, but not limited to, blocking agents, stabilizing agents, detergents, salts, pH buffers, preservatives, etc. Reagents may be present in free form or supported on solid phases including the surfaces of containers (e.g., chambers, channels, flow cells, wells, etc.) in the assay modules or the surfaces of colloids, beads, or other particulate supports. Alternatively or additionally, reagents may be provided in one or more separate vials, containers, or compartments.

The kits and components thereof described herein can be used in any binding assay that involves sample and/or reagent pre-processing. In one embodiment, the kits and components can be used to complete a sample and/or reagent dilution step, e.g., serial dilutions of sample are completed in the integral assembly and then the contents of each container in the assembly are transferred to an assay device or system for further processing. For example, each dilution in the assembly can be assayed in a different well of a multi-well plate and therefore, the visually distinct containers in the assembly are useful to track sample dilutions and the location of each dilution in the corresponding multi-well plate.

Alternatively, the sample or reagent can be pre-mixed with one or more reagents, diluents, buffers, etc. For example, perhaps the user wants to determine the impact of varying buffer concentrations on a particular assay. The user can distribute the sample across the containers of the integral assembly, place the assembly in the receptacle holder, and distribute differing concentrations of buffer across the various sample containers, assigning a different buffer concentration to a unique visual indicator in the assembly. The contents of each container can be transferred to an assay device for further processing once sample pre-treatment is completed.

In yet another embodiment, sample or reagent can be pre-mixed with coated microparticles using the kits and components of the invention. For example, each container in the integral assembly can include a set of coated microparticles or beads to which sample is added. The contents of each container may differ by concentration and/or the addition of one or more addition elements to the assay medium. The pre-treated sample and microparticles can be prepared and mixed in the integral assembly/receptacle holder prior to further assay processing.

In a particularly preferred embodiment, the kits and components of the invention are particularly well suited to assist the user in preparation for conducting a binding assay involving targeting agents and/or targeting agent complements. These components can be used to construct an individually configured multiplexed binding assay for a plurality of target analytes. In this regard, reference is made to copending U.S. Application Ser. No. 61/778,727, the disclosure of which is incorporated herein by reference in its entirety.

FIGS. 3(a)-3(e) and 4(a)-4(e) illustrate assays that can be conducted using the kits and components of the invention. FIGS. 3(a)-3(e) illustrate an indirect binding format for analytes A, B, and C, incorporating a series of linking complexes that allow the user to tailor the assay for his/her needs. FIG. 3(a)-(b) illustrates a general approach for making the targeting complexes used in the assay: a series of solutions are formed that include one of the binding reagents (A', B', and C') bound to a linking agents ($L_A$, $L_B$, and $L_C$, respectively). The solutions also include the corresponding targeting agents, (A" for A', B" for B', and C" for C'), bound to a supplemental linking agent ($L_A'$, $L_B'$, and $L_C'$, respectively). The solutions are mixed, optionally in the kit described herein with each container in the integral assembly used for a distinct analyte, A, B, or C, to form the mixture of binding reagent-linking complex-targeting agent complexes shown in panel (b). The kit can include each of the components of the targeting complexes, i.e., (i) binding reagents, A', B', and C', alone or in combination with (ii) linking agents, $L_A$, $L_B$, and $L_C$, respectively, (iii) the corresponding targeting agents, (A" for A', B" for B', and C" for C'), alone or in combination with (iv) a supplemental linking agent ($L_A'$, $L_B'$, and $L_C'$, respectively), in one or more vials, containers, or compartments. Alternatively, the integral assembly can be provided in the kit with one or more of the targeting components present in the containers of the assembly and the user can add the sample to the containers, as appropriate, using the integral assembly and the receptacle holder. Still further, the integral assembly can be provided in the kit with (i) binding reagents, A', B', and C', alone or in combination with (ii) linking agents, $L_A$, $L_B$, and $L_C$, respectively, and in one or more separate vials, containers, or compartments, (iii) the corresponding targeting agents, (A" for A', B" for B', and C" for C'), alone or in combination with (iv) a supplemental linking agent ($L_A'$, $L_B'$, and $L_C'$, respectively).

As shown in FIG. 3(c)-(e) the mixture of binding reagent-linking complex-targeting agent complexes prepared in the kit and components of the invention are mixed with a surface comprising a plurality of discrete binding domains to which targeting agent complements, A''', B''', and C''' are bound. The binding reagent-linking complex-targeting agent complexes are adsorbed to form binding reagent complexes, $A_{RC}$, $B_{RC}$, and $C_{RC}$ as shown in panel (c). An expanded view of the binding reagent complexes is shown in FIG. 3(e). The surface is contacted with a sample comprising analytes A, B, and C, as well as detection binding reagents, A*, B*, and C*, which are capable of binding to analytes A, B, and C, respectively, and/or a complex comprising those analytes. The detection binding reagents include a detectable label and the detection binding reagents can be provided in the kit in supplemental vial, container, or compartment. Alternatively, the surface is contacted with a sample comprising the plurality of analytes and subsequently contacted with a mixture of detection binding reagents (also optionally provided in the kit in a separate vial, container, or compartment). Once the detection binding reagents are bound to the surface, and optionally, the surface is washed to remove unbound reagents, the presence of each analyte is detected via the detection reagents bound to each discrete binding domain (panel 3(d)). FIGS. 4(a)-4(e) illustrate a specific embodiment of FIGS. 3(a)-3(e) involving the use of antibodies as binding reagents and oligonucleotide-complementary oligonucleotide pairs as targeting agent/targeting agent complement pairs. As noted for FIGS. 3(a)-3(e), the linking agents for each binding reagent may be the same and the linking agent complements for each targeting agent may be the same.

Figure 5A:
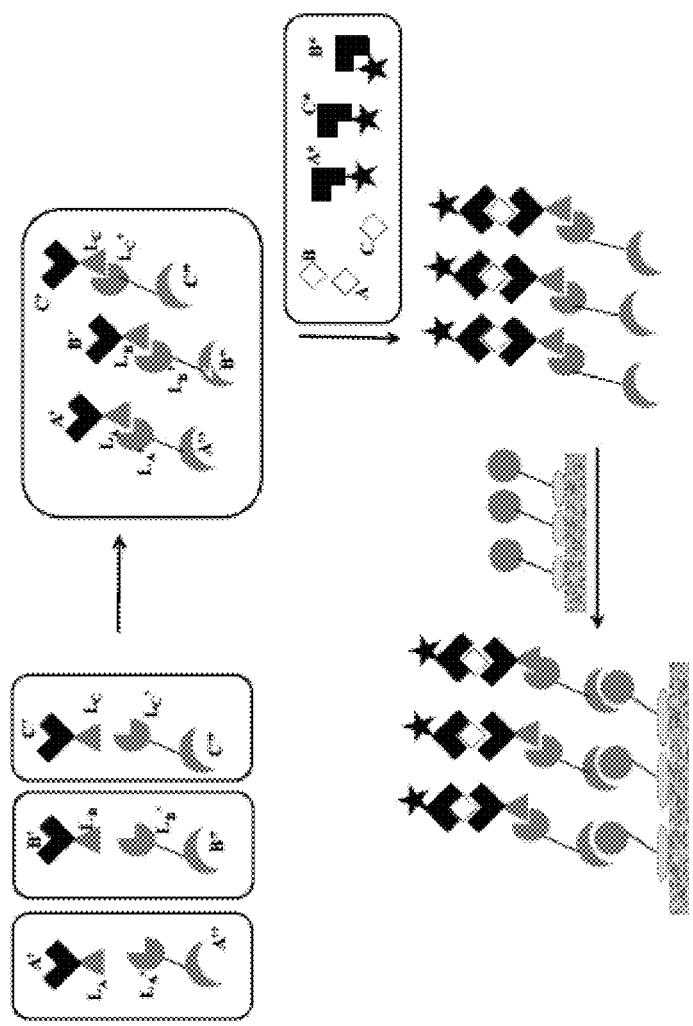

The skilled artisan will readily appreciate that various permutations of the assay format depicted in FIGS. 3(a)-3(e) and 4(a)-4(e) are possible. Certain preferred embodiments are depicted in FIG. 5(a)-(b). For example, binding reagents modified by supplemental linking agents, and targeting agents modified by linking agents can be mixed in a single step in the kit and components of the invention, added to the surface having targeting agent-modified binding domains in a subsequent step, sample and detection reagents are added, and analyzed in a final step (FIG. 5(a)). In yet another embodiment, binding reagents modified by supplemental linking agents, and targeting agent complements modified by linking agents can be mixed in the kit and components of the invention, added to the surface bearing targeting agents in discrete binding domains, mixed with sample, and then detection reagents are added (FIG. 5(b)). Individual analyte solutions can be added to each binding domain sequentially or simultaneously in a single mixture, and likewise, individual detection reagents can be added to each binding domain sequentially or simultaneously in a single mixture. Any surface binding step can optionally be followed by a washing step to remove any unbound components of the assay before proceeding to the next step.

As described in U.S. Provisional Application Ser. No. 62/047,097, filed Sep. 8, 2014, the disclosure of which is incorporated herein by reference in its entirety, the first and second pair of targeting agents comprise a first and second pair of oligonucleotides, respectively, selected from the pairs of sequences listed in Table 1.

TABLE 1(a)

| pair # | Sequence (5'-3') |
|---|---|
| 1 | Acatcggtagtt (SEQ ID NO: 1) |
|   | Aactaccgatgt (SEQ ID NO: 2) |
| 2 | acgtcccagttg (SEQ ID NO: 3) |
|   | caactgggacgt (SEQ ID NO: 4) |
| 3 | agaagaagatcc (SEQ ID NO: 5) |
|   | ggatcttcttct (SEQ ID NO: 6) |
| 4 | aggttcagtgca (SEQ ID NO: 7) |
|   | tgcactgaacct (SEQ ID NO: 8) |
| 5 | atcaggatacgc (SEQ ID NO: 9) |
|   | gcgtatcctgat (SEQ ID NO: 10) |
| 6 | atcattaccacc (SEQ ID NO: 11) |
|   | ggtggtaatgat (SEQ ID NO: 12) |
| 7 | attaacgggagc (SEQ ID NO: 13) |
|   | gctcccgttaat (SEQ ID NO: 14) |
| 8 | cagaggtcttaa (SEQ ID NO: 15) |
|   | ttaagacctctg (SEQ ID NO: 16) |
| 9 | caggtgtccatt (SEQ ID NO: 17) |
|   | aatggacacctg (SEQ ID NO: 18) |
| 10 | catccaatccag (SEQ ID NO: 19) |
|   | ctggattggatg (SEQ ID NO: 20) |
| 11 | cctacgatatac (SEQ ID NO: 21) |
|   | gtatatcgtagg (SEQ ID NO: 22) |
| 12 | cgaatgtagagt (SEQ ID NO: 23) |
|   | actctacattcg (SEQ ID NO: 24) |
| 13 | cggtttgagata (SEQ ID NO: 25) |
|   | tatctcaaaccg (SEQ ID NO: 26) |
| 14 | cttacaacgcca (SEQ ID NO: 27) |
|   | tggcgttgtaag (SEQ ID NO: 28) |
| 15 | ctttctcggcac (SEQ ID NO: 29) |
|   | gtgccgagaaag (SEQ ID NO: 30) |
| 16 | gacataaagcga (SEQ ID NO: 31) |
|   | tcgctttatgtc (SEQ ID NO: 32) |
| 17 | gccatagtctct (SEQ ID NO: 33) |
|   | agagactatggc (SEQ ID NO: 34) |
| 18 | gctaattcacca (SEQ ID NO: 35) |
|   | tggtgaattagc (SEQ ID NO: 36) |
| 19 | ggtcgtgtttca (SEQ ID NO: 37) |
|   | tgaaacacgacc (SEQ ID NO: 38) |

TABLE 1(a)-continued

| pair # | Sequence (5'-3') |
|---|---|
| 20 | gttgattctgtc (SEQ ID NO: 39) |
|   | gacagaatcaac (SEQ ID NO: 40) |
| 21 | tacccggaataa (SEQ ID NO: 41) |
|   | ttattccgggta (SEQ ID NO: 42) |
| 22 | tgcttgacttgg (SEQ ID NO: 43) |
|   | ccaagtcaagca (SEQ ID NO: 44) |
| 23 | ttccacttaggg (SEQ ID NO: 45) |
|   | ccctaagtggaa (SEQ ID NO: 46) |
| 24 | ttgtctagcggc (SEQ ID NO: 47) |
|   | gccgctagacaa (SEQ ID NO: 48) |
| 25 | tttcccttgcta (SEQ ID NO: 49) |
|   | tagcaagggaaa (SEQ ID NO: 50) |

In one embodiment, the targeting agent and the targeting agent complement comprise a pair of oligonucleotides, wherein the pair is selected from one of the following sequence pairs in Table 1(b):

| pair # | Sequence (5'-3') |
|---|---|
| 1 | Acatcggtagtt (SEQ ID NO: 1) |
|   | Aactaccgatgt (SEQ ID NO: 2) |
| 2 | acgtcccagttg (SEQ ID NO: 3) |
|   | caactgggacgt (SEQ ID NO: 4) |
| 3 | agaagaagatcc (SEQ ID NO: 5) |
|   | ggatcttcttct (SEQ ID NO: 6) |
| 4 | aggttcagtgca (SEQ ID NO: 7) |
|   | tgcactgaacct (SEQ ID NO: 8) |
| 5 | atcaggatacgc (SEQ ID NO: 9) |
|   | gcgtatcctgat (SEQ ID NO: 10) |
| 6 | atcattaccacc (SEQ ID NO: 11) |
|   | ggtggtaatgat (SEQ ID NO: 12) |
| 7 | attaacgggagc (SEQ ID NO: 13) |
|   | gctcccgttaat (SEQ ID NO: 14) |
| 8 | cagaggtcttaa (SEQ ID NO: 15) |
|   | ttaagacctctg (SEQ ID NO: 16) |
| 9 | caggtgtccatt (SEQ ID NO: 17) |
|   | aatggacacctg (SEQ ID NO: 18) |
| 10 | catccaatccag (SEQ ID NO: 19) |
|   | ctggattggatg (SEQ ID NO: 20) |
| 11 | cctacgatatac (SEQ ID NO: 21) |
|   | gtatatcgtagg (SEQ ID NO: 22) |

| pair # | Sequence (5'-3') |
|---|---|
| 12 | cgaatgtagagt (SEQ ID NO: 23) |
|  | actctacattcg (SEQ ID NO: 24) |
| 13 | cggtttgagata (SEQ ID NO: 25) |
|  | tatctcaaaccg (SEQ ID NO: 26) |
| 14 | cttacaacgcca (SEQ ID NO: 27) |
|  | tggcgttgtaag (SEQ ID NO: 28) |
| 15 | ctttctcggcac (SEQ ID NO: 29) |
|  | gtgccgagaaag (SEQ ID NO: 30) |
| 16 | gacataaagcga (SEQ ID NO: 31) |
|  | tcgctttatgtc (SEQ ID NO: 32) |
| 17 | gccatagtctct (SEQ ID NO: 33) |
|  | agagactatggc (SEQ ID NO: 34) |
| 18 | gctaattcacca (SEQ ID NO: 35) |
|  | tggtgaattagc (SEQ ID NO: 36) |
| 19 | ggtcgtgtttca (SEQ ID NO: 37) |
|  | tgaaacacgacc (SEQ ID NO: 38) |
| 20 | gttgattctgtc (SEQ ID NO: 39) |
|  | gacagaatcaac (SEQ ID NO: 40) |
| 21 | tacccggaataa (SEQ ID NO: 41) |
|  | ttattccgggta (SEQ ID NO: 42) |
| 22 | tgcttgacttgg (SEQ ID NO: 43) |
|  | ccaagtcaagca (SEQ ID NO: 44) |
| 23 | ttccacttaggg (SEQ ID NO: 45) |
|  | ccctaagtggaa (SEQ ID NO: 46) |
| 24 | ttgtctagcggc (SEQ ID NO: 47) |
|  | gccgctagacaa (SEQ ID NO: 48) |
| 25 | tttcccttgcta (SEQ ID NO: 49) |
|  | tagcaagggaaa (SEQ ID NO: 50) |

In a particular embodiment, the targeting agent and the targeting agent complement comprise a pair of oligonucleotides, wherein the pair is selected from one of the following sequence pairs in Table 1(c):

| Pair | Name | Modification | Sequence |
|---|---|---|---|
| 1 | 3' Thiol Oligo 12b-1 | 3'-thiol C3 SS | acatcggtagtt (SEQ ID NO: 1) |
|  | 3' Biotin Oligo 12b-1 | 3' biotin | aactaccgatgt (SEQ ID NO: 2) |
| 3 | 3' Thiol Oligo 12b-5 | 3'-thiol C3 SS | agaagaagatcc (SEQ ID NO: 5) |
|  | 3' Biotin Oligo 12b-5 | 3' biotin | ggatcttcttct (SEQ ID NO: 6) |
| 6 | 3' Thiol Oligo 12b-12 | 3'-thiol C3 SS | atcattaccacc (SEQ ID NO: 11) |
|  | 3' Biotin Oligo 12b-12 | 3' biotin | ggtggtaatgat (SEQ ID NO: 12) |
| 7 | 3' Thiol Oligo 12b-14 | 3'-thiol C3 SS | attaacgggagc (SEQ ID NO: 13) |
|  | 3' Biotin Oligo 12b-14 | 3' biotin | gctcccgttaat (SEQ ID NO: 14) |
| 8 | 3' Thiol Oligo 12b-17 | 3'-thiol C3 SS | cagaggtcttaa (SEQ ID NO: 15) |
|  | 3' Biotin Oligo 12b-17 | 3' biotin | ttaagacctctg (SEQ ID NO: 16) |
| 9 | 3' Thiol Oligo 12b-18 | 3'-thiol C3 SS | caggtgtccatt (SEQ ID NO: 17) |
|  | 3' Biotin Oligo 12b-18 | 3' biotin | aatggacacctg (SEQ ID NO: 18) |
| 11 | 3' Thiol Oligo 12b-20 | 3'-thiol C3 SS | cctacgatatac (SEQ ID NO: 21) |
|  | 3' Biotin Oligo 12b-20 | 3' biotin | gtatatcgtagg (SEQ ID NO: 22) |
| 12 | 3' Thiol Oligo 12b-21 | 3'-thiol C3 SS | cgaatgtagagt (SEQ ID NO: 23) |
|  | 3' Biotin Oligo 12b-21 | 3' biotin | actctacattcg (SEQ ID NO: 24) |
| 13 | 3' Thiol Oligo 12b-22 | 3'-thiol C3 SS | cggtttgagata (SEQ ID NO: 25) |
|  | 3' Biotin Oligo 12b-22 | 3' biotin | tatctcaaaccg (SEQ ID NO: 26) |
| 16 | 3' Thiol Oligo 12b-26 | 3'-thiol C3 SS | gacataaagcga (SEQ ID NO: 31) |
|  | 3' Biotin Oligo 12b-26 | 3' biotin | tcgctttatgtc (SEQ ID NO: 32) |

-continued

| Pair | Name | Modification | Sequence |
|------|------|--------------|----------|
| 17 | 3' Thiol Oligo 12b-28 | 3'-thiol C3 SS | gccatagtctct (SEQ ID NO: 33) |
|    | 3' Biotin Oligo 12b-28 | 3' biotin | agagactatggc (SEQ ID NO: 34) |
| 18 | 3' Thiol Oligo 12b-30 | 3'-thiol C3 SS | gctaattcacca (SEQ ID NO: 35) |
|    | 3' Biotin Oligo 12b-30 | 3' biotin | tggtgaattagc (SEQ ID NO: 36) |
| 20 | 3' Thiol Oligo 12b-3 | 3 3'-thiol C3 SS | gttgattctgtc (SEQ ID NO: 39) |
|    | 3' Biotin Oligo 12b-33 | 3' biotin | gacagaatcaac (SEQ ID NO: 40) |
| 23 | 3' Thiol Oligo 12b-41 | 3'-thiol C3 SS | ttccacttaggg (SEQ ID NO: 45) |
|    | 3' Biotin Oligo 12b-41 | 3' biotin | ccctaagtggaa (SEQ ID NO: 46) |
| 25 | 3' Thiol Oligo 12b-43 | 3'-thiol C3 SS | tttcccttgcta (SEQ ID NO: 49) |
|    | 3' Biotin Oligo 12b-43 | 3' biotin | tagcaagggaaa (SEQ ID NO: 50) |

For example, the invention includes one of the sets of ten pair of targeting agent and the targeting agent complement shown in Table 1(d):

| 3' Thiol Oligo | Corresponding 3' Biotinylated Oligo |
|----------------|-------------------------------------|
| Set (1) | |
| 5'- ATC ATT ACC ACC /3ThioMC3-D/-3' (SEQ ID NO: 11) | 5'- GGT GGT AAT GAT /3Bio/-3' (SEQ ID NO: 12) |
| 5'- CCT ACG ATA TAC /3ThioMC3-D/-3' (SEQ ID NO: 21) | 5'- GTA TAT CGT AGG /3Bio/-3' (SEQ ID NO: 22) |
| 5'- CGG TTT GAG ATA /3ThioMC3-D/-3' (SEQ ID NO: 25) | 5'- TAT CTC AAA CCG /3Bio/-3' (SEQ ID NO: 26) |
| 5'- GAC ATA AAG CGA /3ThioMC3-D/-3' (SEQ ID NO: 31) | 5'- TCG CTT TAT GTC /3Bio/-3' (SEQ ID NO: 32) |
| 5'- GTT GAT TCT GTC /3ThioMC3-D/-3' (SEQ ID NO: 39) | 5'- GAC AGA ATC AAC /3Bio/-3' (SEQ ID NO: 40) |
| 5'- GCT AAT TCA CCA /3ThioMC3-D/-3' (SEQ ID NO: 35) | 5'- TGG TGA ATT AGC /3Bio/-3' (SEQ ID NO: 36) |
| 5'- TTT CCC TTG CTA /3ThioMC3-D/-3' (SEQ ID NO: 49) | 5'- TAG CAA GGG AAA /3Bio/-3' (SEQ ID NO: 50) |
| 5'- AGA AGA AGA TCC /3ThioMC3-D/-3' (SEQ ID NO: 5) | 5'- GGA TCT TCT TCT /3Bio/-3' (SEQ ID NO: 6) |
| 5'- ACA TCG GTA GTT /3ThioMC3-D/-3' (SEQ ID NO: 1) | 5'- AAC TAC CGA TGT /3Bio/-3' (SEQ ID NO: 2) |
| 5'- GCC ATA GTC TCT /3ThioMC3-D/-3' (SEQ ID NO: 33) | 5'- AGA GAC TAT GGC /3Bio/-3' (SEQ ID NO: 34) |
| Set (2) | |
| 5'- CGA ATG TAG AGT /3ThioMC3-D/-3' (SEQ ID NO: 23) | 5'- ACT CTA CAT TCG /3Bio/-3' (SEQ ID NO: 24) |
| 5'- TTC CAC TTA GGG /3ThioMC3-D/-3' (SEQ ID NO: 45) | 5'- CCC TAA GTG GAA /3Bio/-3' (SEQ ID NO: 46) |
| 5'- CAG AGG TCT TAA /3ThioMC3-D/-3' (SEQ ID NO: 15) | 5'- TTA AGA CCT CTG /3Bio/-3' (SEQ ID NO: 16) |
| 5'- ACG TCC CAG TTG /3ThioMC3-D/-3' (SEQ ID NO: 3) | 5'- CAA CTG GGA CGT /3Bio/-3' (SEQ ID NO: 4) |

-continued

| 3' Thiol Oligo | Corresponding 3' Biotinylated Oligo |
|---|---|
| 5'- AGG TTC AGT GCA /3ThioMC3-D/-3'<br>(SEQ ID NO: 7) | 5'- TGC ACT GAA CCT /3Bio/-3'<br>(SEQ ID NO: 8) |
| 5'- ATC AGG ATA CGC /3ThioMC3-D/-3'<br>(SEQ ID NO: 9) | 5'- GCG TAT CCT GAT /3Bio/-3'<br>(SEQ ID NO: 10) |
| 5'- CAT CCA ATC CAG /3ThioMC3-D/-3'<br>(SEQ ID NO: 19) | 5'- CTG GAT TGG ATG /3Bio/-3'<br>(SEQ ID NO: 20) |
| 5'- CTT ACA ACG CCA /3ThioMC3-D/-3'<br>(SEQ ID NO: 27) | 5'- TGG CGT TGT AAG /3Bio/-3'<br>(SEQ ID NO: 28) |
| 5'- CTT TCT CGG CAC /3ThioMC3-D/-3'<br>(SEQ ID NO: 29) | 5'- GTG CCG AGA AAG /3Bio/-3'<br>(SEQ ID NO: 30) |
| 5'- GGT CGT GTT TCA /3ThioMC3-D/-3'<br>(SEQ ID NO: 37) | 5'- TGA AAC ACG ACC /3Bio/-3'<br>(SEQ ID NO: 38) |
| Set (3) | |
| 5'- ATT AAC GGG AGC /3ThioMC3-D/-3'<br>(SEQ ID NO: 13) | 5'- GCT CCC GTT AAT /3Bio/-3'<br>(SEQ ID NO: 14) |
| 5'- CAG GTG TCC ATT /3ThioMC3-D/-3'<br>(SEQ ID NO: 17) | 5'- AAT GGA CAC CTG /3Bio/-3'<br>(SEQ ID NO: 18) |
| 5'- CGA ATG TAG AGT /3ThioMC3-D/-3'<br>(SEQ ID NO: 23) | 5'- ACT CTA CAT TCG /3Bio/-3'<br>(SEQ ID NO: 24) |
| 5'- TTC CAC TTA GGG /3ThioMC3-D/-3'<br>(SEQ ID NO: 45) | 5'- CCC TAA GTG GAA /3Bio/-3'<br>(SEQ ID NO: 46) |
| 5'- CAG AGG TCT TAA /3ThioMC3-D/-3'<br>(SEQ ID NO: 15) | 5'- TTA AGA CCT CTG /3Bio/-3'<br>(SEQ ID NO: 16) |
| 5'- ACG TCC CAG TTG /3ThioMC3-D/-3'<br>(SEQ ID NO: 3) | 5'- CAA CTG GGA CGT /3Bio/-3'<br>(SEQ ID NO: 4) |
| 5'- AGG TTC AGT GCA /3ThioMC3-D/-3'<br>(SEQ ID NO: 7) | 5'- TGC ACT GAA CCT /3Bio/-3'<br>(SEQ ID NO: 8) |
| 5'- ATC AGG ATA CGC /3ThioMC3-D/-3'<br>(SEQ ID NO: 9) | 5'- GCG TAT CCT GAT /3Bio/-3'<br>(SEQ ID NO: 10) |
| 5'- CAT CCA ATC CAG /3ThioMC3-D/-3'<br>(SEQ ID NO: 19) | 5'- CTG GAT TGG ATG /3Bio/-3'<br>(SEQ ID NO: 20) |
| 5'- CTT ACA ACG CCA /3ThioMC3-D/-3'<br>(SEQ ID NO: 27) | 5'- TGG CGT TGT AAG /3Bio/-3'<br>(SEQ ID NO: 28) |
| Set (4) | |
| 5'- GCT AAT TCA CCA /3ThioMC3-D/-3'<br>(SEQ ID NO: 35) | 5'- TGG TGA ATT AGC /3Bio/-3'<br>(SEQ ID NO: 36) |
| 5'- TTT CCC TTG CTA /3ThioMC3-D/-3'<br>(SEQ ID NO: 49) | 5'- TAG CAA GGG AAA /3Bio/-3'<br>(SEQ ID NO: 50) |
| 5'- AGA AGA AGA TCC /3ThioMC3-D/-3'<br>(SEQ ID NO: 5) | 5'- GGA TCT TCT TCT /3Bio/-3'<br>(SEQ ID NO: 6) |
| 5'- ACA TCG GTA GTT /3ThioMC3-D/-3'<br>(SEQ ID NO: 1) | 5'- AAC TAC CGA TGT /3Bio/-3'<br>(SEQ ID NO: 2 |
| 5'- GCC ATA GTC TCT /3ThioMC3-D/-3'<br>(SEQ ID NO: 33) | 5'- AGA GAC TAT GGC /3Bio/-3'<br>(SEQ ID NO: 34) |
| 5'- ATT AAC GGG AGC /3ThioMC3-D/-3'<br>(SEQ ID NO: 13) | 5'- GCT CCC GTT AAT /3Bio/-3'<br>(SEQ ID NO: 14) |
| 5'- CAG GTG TCC ATT /3ThioMC3-D/-3'<br>(SEQ ID NO: 17) | 5'- AAT GGA CAC CTG /3Bio/-3'<br>(SEQ ID NO: 18) |
| 5'- CGA ATG TAG AGT /3ThioMC3-D/-3'<br>(SEQ ID NO: 23) | 5'- ACT CTA CAT TCG /3Bio/-3'<br>(SEQ ID NO: 24) |

-continued

| 3' Thiol Oligo | Corresponding 3' Biotinylated Oligo |
|---|---|
| 5'- TTC CAC TTA GGG /3ThioMC3-D/-3' (SEQ ID NO: 45) | 5'- CCC TAA GTG GAA /3Bio/-3' (SEQ ID NO: 46) |
| 5'- CAG AGG TCT TAA /3ThioMC3-D/-3' (SEQ ID NO: 15) | 5'- TTA AGA CCT CTG /3Bio/-3' (SEQ ID NO: 16) |

Set (5)

| | |
|---|---|
| 5'- ATC ATT ACC ACC /3ThioMC3-D/-3' (SEQ ID NO: 11) | 5'- GGT GGT AAT GAT /3Bio/-3' (SEQ ID NO: 12) |
| 5'- CCT ACG ATA TAC /3ThioMC3-D/-3' (SEQ ID NO: 21) | 5'- GTA TAT CGT AGG /3Bio/-3' (SEQ ID NO: 22) |
| 5'- CGG TTT GAG ATA /3ThioMC3-D/-3' (SEQ ID NO: 25) | 5'- TAT CTC AAA CCG /3Bio/-3' (SEQ ID NO: 26) |
| 5'- GAC ATA AAG CGA /3ThioMC3-D/-3' (SEQ ID NO: 31) | 5'- TCG CTT TAT GTC /3Bio/-3' (SEQ ID NO: 32) |
| 5'- GTT GAT TCT GTC /3ThioMC3-D/-3' (SEQ ID NO: 39) | 5'- GAC AGA ATC AAC /3Bio/-3' (SEQ ID NO: 40) |
| 5'- ATC AGG ATA CGC /3ThioMC3-D/-3' (SEQ ID NO: 9) | 5'- GCG TAT CCT GAT /3Bio/-3' (SEQ ID NO: 10) |
| 5'- CAT CCA ATC CAG /3ThioMC3-D/-3' (SEQ ID NO: 19) | 5'- CTG GAT TGG ATG /3Bio/-3' (SEQ ID NO: 20) |
| 5'- CTT ACA ACG CCA /3ThioMC3-D/-3' (SEQ ID NO: 27) | 5'- TGG CGT TGT AAG /3Bio/-3' (SEQ ID NO: 28) |
| 5'- CTT TCT CGG CAC /3ThioMC3-D/-3' (SEQ ID NO: 29) | 5'- GTG CCG AGA AAG /3Bio/-3' (SEQ ID NO: 30) |
| 5'- GGT CGT GTT TCA /3ThioMC3-D/-3' (SEQ ID NO: 37) | 5'- TGA AAC ACG ACC /3Bio/-3' (SEQ ID NO: 38) |

Set (6)

| | |
|---|---|
| 5'- ATC ATT ACC ACC /3ThioMC3-D/-3' (SEQ ID NO: 11) | 5'- GGT GGT AAT GAT /3Bio/-3' (SEQ ID NO: 12) |
| 5'- CCT ACG ATA TAC /3ThioMC3-D/-3' (SEQ ID NO: 21) | 5'- GTA TAT CGT AGG /3Bio/-3' (SEQ ID NO: 22) |
| 5'- GAC ATA AAG CGA /3ThioMC3-D/-3' (SEQ ID NO: 31) | 5'- TCG CTT TAT GTC /3Bio/-3' (SEQ ID NO: 32) |
| 5'- GTT GAT TCT GTC /3ThioMC3-D/-3' (SEQ ID NO: 39) | 5'- GAC AGA ATC AAC /3Bio/-3' (SEQ ID NO: 40) |
| 5'- AGA AGA AGA TCC /3ThioMC3-D/-3' (SEQ ID NO: 5) | 5'- GGA TCT TCT TCT /3Bio/-3' (SEQ ID NO: 6) |
| 5'- ACA TCG GTA GTT /3ThioMC3-D/-3' (SEQ ID NO: 1) | 5'- AAC TAC CGA TGT /3Bio/-3' (SEQ ID NO: 2) |
| 5'- CAG GTG TCC ATT /3ThioMC3-D/-3' (SEQ ID NO: 17) | 5'- AAT GGA CAC CTG /3Bio/-3' (SEQ ID NO: 18) |
| 5'- CGA ATG TAG AGT /3ThioMC3-D/-3' (SEQ ID NO: 23) | 5'- ACT CTA CAT TCG /3Bio/-3' (SEQ ID NO: 24) |
| 5'- ACG TCC CAG TTG /3ThioMC3-D/-3' (SEQ ID NO: 3) | 5'- CAA CTG GGA CGT /3Bio/-3' (SEQ ID NO: 4) |
| 5'- AGG TTC AGT GCA /3ThioMC3-D/-3' (SEQ ID NO: 7) | 5'- TGC ACT GAA CCT /3Bio/-3' (SEQ ID NO: 8) |

Set (7)

| | |
|---|---|
| 5'- CGG TTT GAG ATA /3ThioMC3-D/-3' (SEQ ID NO: 25) | 5'- TAT CTC AAA CCG /3Bio/-3' (SEQ ID NO: 26) |
| 5'- GAC ATA AAG CGA /3ThioMC3-D/-3' (SEQ ID NO: 31) | 5'- TCG CTT TAT GTC /3Bio/-3' (SEQ ID NO: 32) |

-continued

| 3' Thiol Oligo | Corresponding 3' Biotinylated Oligo |
|---|---|
| 5'- TTT CCC TTG CTA /3ThioMC3-D/-3' (SEQ ID NO: 49) | 5'- TAG CAA GGG AAA /3Bio/-3' (SEQ ID NO: 50) |
| 5'- AGA AGA AGA TCC /3ThioMC3-D/-3' (SEQ ID NO: 5) | 5'- GGA TCT TCT TCT /3Bio/-3' (SEQ ID NO: 6) |
| 5'- ATT AAC GGG AGC /3ThioMC3-D/-3' (SEQ ID NO: 13) | 5'- GCT CCC GTT AAT /3Bio/-3' (SEQ ID NO: 14) |
| 5'- CAG GTG TCC ATT /3ThioMC3-D/-3' (SEQ ID NO: 17) | 5'- AAT GGA CAC CTG /3Bio/-3' (SEQ ID NO: 18) |
| 5'- TTC CAC TTA GGG /3ThioMC3-D/-3' (SEQ ID NO: 45) | 5'- CCC TAA GTG GAA /3Bio/-3' (SEQ ID NO: 46) |
| 5'- CAG AGG TCT TAA /3ThioMC3-D/-3' (SEQ ID NO: 15) | 5'- TTA AGA CCT CTG /3Bio/-3' (SEQ ID NO: 16) |
| 5'- ATC AGG ATA CGC /3ThioMC3-D/-3' (SEQ ID NO: 9) | 5'- GCG TAT CCT GAT /3Bio/-3' (SEQ ID NO: 10) |
| 5'- CAT CCA ATC CAG /3ThioMC3-D/-3' (SEQ ID NO: 19) | 5'- CTG GAT TGG ATG /3Bio/-3' (SEQ ID NO: 20) |

Set (8)

| 5'- GCT AAT TCA CCA /3ThioMC3-D/-3' (SEQ ID NO: 35) | 5'- TGG TGA ATT AGC /3Bio/-3' (SEQ ID NO: 36) |
|---|---|
| 5'- TTT CCC TTG CTA /3ThioMC3-D/-3' (SEQ ID NO: 49) | 5'- TAG CAA GGG AAA /3Bio/-3' (SEQ ID NO: 50) |
| 5'- AGA AGA AGA TCC /3ThioMC3-D/-3' (SEQ ID NO: 5) | 5'- GGA TCT TCT TCT /3Bio/-3' (SEQ ID NO: 6) |
| 5'- ACA TCG GTA GTT /3ThioMC3-D/-3' (SEQ ID NO: 1) | 5'- AAC TAC CGA TGT /3Bio/-3' (SEQ ID NO: 2) |
| 5'- GCC ATA GTC TCT /3ThioMC3-D/-3' (SEQ ID NO: 33) | 5'- AGA GAC TAT GGC /3Bio/-3' (SEQ ID NO: 34) |
| 5'- ACG TCC CAG TTG /3ThioMC3-D/-3' (SEQ ID NO: 3) | 5'- CAA CTG GGA CGT /3Bio/-3' (SEQ ID NO: 4) |
| 5'- AGG TTC AGT GCA /3ThioMC3-D/-3' (SEQ ID NO: 7) | 5'- TGC ACT GAA CCT /3Bio/-3' (SEQ ID NO: 8) |
| 5'- ATC AGG ATA CGC /3ThioMC3-D/-3' (SEQ ID NO: 9) | 5'- GCG TAT CCT GAT /3Bio/-3' (SEQ ID NO: 10) |
| 5'- CAT CCA ATC CAG /3ThioMC3-D/-3' (SEQ ID NO: 19) | 5'- CTG GAT TGG ATG /3Bio/-3' (SEQ ID NO: 20) |
| 5'- CTT ACA ACG CCA /3ThioMC3-D/-3' (SEQ ID NO: 27) | 5'- TGG CGT TGT AAG /3Bio/-3' (SEQ ID NO: 28) |

Set (9)

| 5'- ATT AAC GGG AGC /3ThioMC3-D/-3' (SEQ ID NO: 13) | 5'- GCT CCC GTT AAT /3Bio/-3' (SEQ ID NO: 14) |
|---|---|
| 5'- CAG GTG TCC ATT /3ThioMC3-D/-3' (SEQ ID NO: 17) | 5'- AAT GGA CAC CTG /3Bio/-3' (SEQ ID NO: 18) |
| 5'- CGA ATG TAG AGT /3ThioMC3-D/-3' (SEQ ID NO: 23) | 5'- ACT CTA CAT TCG /3Bio/-3' (SEQ ID NO: 24) |
| 5'- TTC CAC TTA GGG /3ThioMC3-D/-3' (SEQ ID NO: 45) | 5'- CCC TAA GTG GAA /3Bio/-3' (SEQ ID NO: 46) |
| 5'- CAG AGG TCT TAA /3ThioMC3-D/-3' (SEQ ID NO: 15) | 5'- TTA AGA CCT CTG /3Bio/-3' (SEQ ID NO: 16) |
| 5'- ATC AGG ATA CGC /3ThioMC3-D/-3' (SEQ ID NO: 9) | 5'- GCG TAT CCT GAT /3Bio/-3' (SEQ ID NO: 10) |

-continued

| 3' Thiol Oligo | Corresponding 3' Biotinylated Oligo |
|---|---|
| 5'- CAT CCA ATC CAG /3ThioMC3-D/-3' (SEQ ID NO: 19) | 5'- CTG GAT TGG ATG /3Bio/-3' (SEQ ID NO: 20) |
| 5'- CTT ACA ACG CCA /3ThioMC3-D/-3' (SEQ ID NO: 27) | 5'- TGG CGT TGT AAG /3Bio/-3' (SEQ ID NO: 28) |
| 5'- CTT TCT CGG CAC /3ThioMC3-D/-3' (SEQ ID NO: 29) | 5'- GTG CCG AGA AAG /3Bio/-3' (SEQ ID NO: 30) |
| 5'- GGT CGT GTT TCA /3ThioMC3-D/-3' (SEQ ID NO: 37) | 5'- TGA AAC ACG ACC /3Bio/-3' (SEQ ID NO: 38) |
| Set (10) | |
| 5'- GAC ATA AAG CGA /3ThioMC3-D/-3' (SEQ ID NO: 31) | 5'- TCG CTT TAT GTC /3Bio/-3' (SEQ ID NO: 32) |
| 5'- GTT GAT TCT GTC /3ThioMC3-D/-3' (SEQ ID NO: 39) | 5'- GAC AGA ATC AAC /3Bio/-3' (SEQ ID NO: 40) |
| 5'- GCT AAT TCA CCA /3ThioMC3-D/-3' (SEQ ID NO: 35) | 5'- TGG TGA ATT AGC /3Bio/-3' (SEQ ID NO: 36) |
| 5'- TTT CCC TTG CTA /3ThioMC3-D/-3' (SEQ ID NO: 49) | 5'- TAG CAA GGG AAA /3Bio/-3' (SEQ ID NO: 50) |
| 5'- AGA AGA AGA TCC /3ThioMC3-D/-3' (SEQ ID NO: 5) | 5'- GGA TCT TCT TCT /3Bio/-3' (SEQ ID NO: 6) |
| 5'- TTC CAC TTA GGG /3ThioMC3-D/-3' (SEQ ID NO: 45) | 5'- CCC TAA GTG GAA /3Bio/-3' (SEQ ID NO: 46) |
| 5'- CAG AGG TCT TAA /3ThioMC3-D/-3' (SEQ ID NO: 15) | 5'- TTA AGA CCT CTG /3Bio/-3' (SEQ ID NO: 16) |
| 5'- ACG TCC CAG TTG /3ThioMC3-D/-3' (SEQ ID NO: 3) | 5'- CAA CTG GGA CGT /3Bio/-3' (SEQ ID NO: 4) |
| 5'- AGG TTC AGT GCA /3ThioMC3-D/-3' (SEQ ID NO: 7) | 5'- TGC ACT GAA CCT /3Bio/-3' (SEQ ID NO: 8) |
| 5'- ATC AGG ATA CGC /3ThioMC3-D/-3' (SEQ ID NO: 9) | 5'- GCG TAT CCT GAT /3Bio/-3' (SEQ ID NO: 10) |

In a specific embodiment, the set comprises set 1 listed in Table 1(d). Alternatively, the set comprises set 2 from Table 1(d); the set can also comprise set 3 from Table 1(d); the set further comprises set 4 from Table 1(d); the set also includes set 5 from Table 1(d); the set includes set 6 from Table 1(d); the set further comprises set 7 from Table 1(d); the set can also include set 8 from Table 1(d); the set includes set 9 from Table 1(d); and/or the set includes set 10 from Table 1(d).

The kit further includes, in separate vials, containers, or compartments, at least 4 oligonucleotides comprising a different sequence selected from the sequences listed in Table 1. These sequences may include four sequences selected from different pairs or may include more than one member of a pair.

The kit can include at least 7, 10, 16, or 25 surface bound oligonucleotides and corresponding oligonucleotide complements. The oligonucleotides configured for use as targeting agent complements can be provided pre-bound to a binding reagent such as an antibody or can be provided modified with a linking agent for attachment to a binding reagent by the user. Optionally, each oligonucleotide complement in the kit is coupled to a different binding reagent, e.g., antibody. The surface-bound oligonucleotides can be incorporated into an array comprising a plurality of at least 5 (7, 10, 16, or 25) oligonucleotides immobilized to each binding domain such that a different oligonucleotide sequence is immobilized to a discrete binding domain. In a specific embodiment, a multi-well plate can include one or more copies of an oligonucleotide array as described herein within at least one well of the plate, wherein the array is positioned on a plurality of binding domains. The plate can include at least 24, 96, or 384 wells and the array can include at least 7 oligonucleotides, or at least 10, 16, or 25 oligonucleotides.

In a specific embodiment, the kit includes a multi-well plate having one or more copies of an oligonucleotide array within at least one well(s) of the plate, the array is positioned on a plurality of binding domains, wherein at least 4 of the binding domains have immobilized thereon a different oligonucleotide sequence selected from a different sequence pair from the set of sequence pairs listed in Table 1(a)-(d). The kit may further comprise an additional set of oligonucleotides comprised of two or more oligonucleotides selected from the set of sequences in Table 1(a)-(d), wherein the additional oligonucleotides are complementary to the immobilized oligonucleotides. In a specific embodiment, the invention provides a kit comprising: (a) a multi-well plate comprising a plurality of discrete binding domains each comprising a first and second oligonucleotide, respectively, each of said first and second oligonucleotides are selected from the group consisting of the sequences listed in Table 1(a)-(d).

The kit can also include instructions for use of the multi-well plate in a method of conducting a binding assay for a plurality of analytes, said method comprising the steps of:

(a) forming a first binding reagent complex comprising a first binding reagent specific for a first analyte in said plurality of analytes and said first oligonucleotide, wherein said first binding reagent is bound to a linking agent and said first oligonucleotide is bound to a supplemental linking agent wherein said first binding reagent complex is formed by a reaction between said linking agent and said supplemental linking agent;

(b) forming a second binding reagent complex comprising a second binding reagent specific for a second analyte in said plurality of analytes and said second oligonucleotide, wherein said second binding reagent is bound to a second linking agent and said second oligonucleotide is bound to a second supplemental linking agent wherein said second binding reagent complex is formed by a reaction between said second linking agent and said second supplemental linking agent;

(c) mixing said first and second binding reagent complexes with said two or more binding domains each linked to a first oligonucleotide complement and a second oligonucleotide complement, respectively, under conditions sufficient to bind said first oligonucleotide to said first oligonucleotide complement and said second oligonucleotide to said second oligonucleotide complement;

(d) mixing a sample comprising said plurality of analytes to the mixture formed in step (c);

(e) adding a plurality of additional binding reagents to the mixture formed in step (d), wherein said plurality of additional binding reagents includes (i) a first detection reagent specific for said first analyte and/or a first binding reagent-first analyte complex; and (ii) a second detection reagent specific for said second analyte and/or a second binding reagent-second analyte complex; and (f) measuring the amount of said first and second analytes bound to said binding domains.

In one specific embodiment, a multi-well assay plate can be used to configure an end-user developed assay panel, i.e., an assay panel built by the end-user with his/her binding reagents to conduct an assay with the plate. In this embodiment, the end-user designates which binding reagent is bound to each binding domain. A multi-well assay plate is provided that includes a plurality of discrete binding domains including a first binding domain with a first targeting agent and a second binding domain with a second targeting agent and, optionally, additional binding domains with additional targeting agents. Each of the binding domains are functionalized by the user by selecting individual binding reagents that will be attached to each of the plurality of binding domains via a binding reagent complex, as described herein. In a separate vial, container, or compartment, a set of targeting reagents (each attached to a linking agent) is provided that includes a first targeting agent complement, a second targeting agent complement, and optionally additional targeting agent complements. The first targeting agent and first targeting agent complement and the second targeting agent and second targeting agent complement constitute a first and second pair of targeting agents, respectively. Similarly, any additional targeting agent complements form pairs with the different additional targeting agents on the binding domains. In one preferred embodiment, the targeting agents and targeting agent complements are oligonucleotides (i.e., an oligonucleotide and its complement). In this embodiment, the first and second pairs of targeting agents, and any additional pairs of targeting agents, are selected from the list of sequences provided in Table 1(a)-(d).

Therefore, the user selects which targeting agent/targeting agent complement will be bound to each specific binding domain. The user also selects which binding reagent will be bound to each specific binding domain and forms a binding reagent complex that includes the targeting agent complement of the targeting agent attached to the designated binding domain.

The kit may provide reagents for the users to attach the supplementary linking agent to the users' binding reagents. When biotin is the supplementary linking agent, the kit may include biotin modified with a reactive functional group such as an NHS ester or hydrazide or maleimide. The plate and/or set of targeting reagents can further include a labeling kit for attaching a detectable label to an assay component, such as a detection reagent. For example, if the multi-well assay plate is configured to conduct an electrochemiluminescence reaction, the labeling kit can include a SULFO-TAG™ NHS ester, LC-biotin NHS ester, an optional spin column, and optional labeling buffer solution. Further provided can be ECL read buffer and optional assay and antibody diluents.

The set of targeting reagents preferably includes a quantity of targeting reagents that matches the number of binding domains present in the multi-well plate. For example, if the multi-well plate includes ten discrete binding domains, a set of 10 targeting reagents are used with that multi-well plate.

The targeting agents may be provided with a linking agent that directly binds to the supplementary linking agent, e.g., streptavidin or avidin when the supplementary linking agent is biotin. When the linking agent and supplementary linking agent are configured to be linked through a bridging agent (e.g., when both the linking and supplementary linking agents are biotin), the kit may also provide a bridging reagent solution (e.g., a solution of streptavidin or avidin) that can be used to attach the binding reagent to the targeting agent complement. The kit may also provide a reaction buffer that provides the appropriate conditions for the linking/bridging reactions and a reaction stop solution. When one or more of the linking reagents are biotin, the stop solution may include free biotin to block any unused biotin-binding sites in streptavidin or avidin that is present as a linking agent, supplemental linking agent or bridging agent.

In this embodiment, the user supplies the binding reagents, e.g., capture and detection antibodies, and designates which binding reagent will be attached to each of the binding domains. The binding reagent, e.g., capture antibody, is labeled with a selected linking agent, e.g., biotin, and attached to a member of a targeting agent pair via a supplemental linking agent, e.g., streptavidin. Meanwhile, the plate is prepared by binding the targeting agent to the selected binding domain. The modified binding reagent contacts the surface to form a surface-bound binding reagent complex that can be used in a subsequent binding assay for an analyte recognized by the binding reagent. The analyte of interest is detected by contacting the binding domain with a labeled binding reagent and measuring the presence of the label present at that binding domain.

Alternatively, a multi-well assay plate can be configured based on a user's specifications, e.g., from a catalog of available multiplexed assay panels and/or a user can select a set of analytes to configure a user-customized multiplexed assay for that set of analytes. A multiplexed assay panel should be selected and optimized such that individual assays function well together. For example, the sample may require dilution prior to being assayed. Sample dilutions for specific sample matrices of interest are optimized for a given panel to minimize sample matrix effects and to maximize the likelihood that all the analytes in the panel will be within the dynamic range of the assay. In a preferred embodiment, all of the analytes in the panel are analyzed with the same sample dilution in at least one sample type. In another preferred embodiment, all of the analytes in a panel are measured using the same dilution for most sample types.

These and other embodiments of the invention are illustrated in the following non-limited examples.

EXAMPLES

Example 1

Assay Reagent Preparation & Assay Protocol (a) Reagent Preparation

Linkers (200 uL each) are provided in the strip of tubes illustrated in FIGS. 1(a)-1(e). No dilution is required. Each strip of tubes is tapped gently to ensure that all linker solutions fall to the bottom of the tubes. The strip of the tubes is inserted into the receptacle holder depicted in FIGS. 2(a) and 2(b).

Antibody solutions are prepared by diluting antibody stock solution to the recommended concentration with MSD diluent, available from Meso Scale Discovery, a division of Meso Scale Diagnostics, Rockville, Md., and adding antibody solution to a tube in the strip of tubes. For one 96-well MULTI-SPOT® assay plate (also available from Meso Scale Discovery), at least 200 uL of each antibody solution is prepared and added to each tube in the strip of tubes. Therefore, each tube includes a linker mixed with an antibody solution.

Add at least 2000 uL Stop Solution (available from Meso Scale Discovery) to a fluid reservoir. No dilution is required and one 96-well plate requires at least 2000 uL stop solution.

(b) Prepare Information Card

Each antibody is assigned a color which corresponds to a spot on the plate. Write assay names next to the colored circles on the information card and insert the card into the cover of the receptacle holder.

(c) Assay Protocol

Cap the tubes including antibody and linker and vortex briefly. Incubate for 30 minutes without shaking at room temperature. Add 200 uL of Stop Solution to each tube. Cap the tubes, vortex briefly, and incubate for 30 minutes without shaking at room temperature. Use a multi-channel pipette to aspirate 550 uL from each tube and dispense all the solution into the fluid reservoir. Pipette to mix the solution in the tray. Add 50 uL of the mixed solution to each well of the multi-well assay plate. Seal the plate with an adhesive plate seal and incubate, with shaking, for 1 hour at room temperature. Wash the plate three times with wash buffer (available from Meso Scale Discovery), and a set of labeled detection antibodies (50 uL of MSD Diluent 3; Meso Scale Discovery) is added to each well of the multi-well plate. The plate is incubated with shaking and the wells are washed with 3×PBS, filled with 150 uL of Read Buffer T (Meso Scale Discovery) and analyzed on a SECTOR® Imager instrument.

The present invention is not to be limited in scope by the specific embodiments described herein. Indeed, various modifications of the method in addition to those described herein will become apparent to those skilled in the art from the foregoing description and accompanying figures. Such modifications are intended to fall within the scope of the claims. Various publications are cited herein, the disclosures of which are incorporated by reference in their entireties.

What is claimed is:

1. A kit comprising:
    (a) an integral assembly of a plurality of spaced containers arranged in an aligned series, wherein each container includes a visual indicator to distinguish a container in the plurality from an additional container in the plurality, wherein only a single spaced container at one end of the aligned series of the plurality of spaced containers comprises (i) a protrusion that extends from a top end to a bottom end of the single spaced container, or (ii) a shape that differs from the remainder of the containers in the plurality of spaced containers, wherein the plurality of spaced containers are arranged in an elongated uninterrupted strip; and
    (b) a holder comprising (i) a top surface and a top surface support; (ii) a plurality of openings positioned on the top surface and configured to receive the integral assembly of containers, wherein, only one of the plurality of openings, at one end of the plurality of openings, is of a different shape than the other plurality of openings and is configured to accommodate the protrusion or the shape of the single spaced container, wherein the plurality of openings correspond to the configuration of a plurality of the integral assembly of containers, and wherein the protrusion or the shape is configured to insure that the plurality of integral assembly cannot be inserted into the holder unless they are positioned in the correct orientation.

2. The kit of claim 1 wherein the containers comprise vials, test tubes, microtube tubes, or combinations thereof.

3. The kit of claim 1 wherein the containers comprise microtube tubes.

4. The kit of claim 1 wherein the visual indicator comprises a pattern or color.

5. The kit of claim 4 wherein the visual indicator comprises a color.

6. The kit of claim 1 wherein the plurality of openings is arranged in an array.

7. The kit of claim 6 wherein the array comprises a 1×10, 2×10; 3×10, 4×10, 5×10, 6×10, 7×10, 8×10, 9×10, or 10×10 array of openings.

8. The kit of claim 6 wherein the array comprises a 1×4, 2×4, 3×4, 4×4, 5×4, 6×4, 7×4, 8×4, 9×4, or 10×4 array of openings.

9. The kit of claim 6 wherein the array comprises a 1×7, 2×7, 3×7, 4×7, 5×7, 6×7, 7×7, 8×7, 9×7, or 10×7 array of openings.

10. The kit of claim 6 wherein the array comprises a 1×16, 2×16, 3×16, 4×16, 5×16, 6×16, 7×16, 8×16, 9×16, or 10×16 array of openings.

11. The kit of claim 6 wherein the array comprises a 1×25, 2×25, 3×25 4×25, 5×25, 6×25, 7×25, 8×25, 9×25, or 10×25 array of openings.

12. The kit of claim 7 wherein the array comprises a 5×10 array of openings.

13. The kit of claim 7 wherein the integral assembly comprises up to 10 spaced containers.

14. The kit of claim 8 wherein the integral assembly comprises up to 4 spaced containers.

15. The kit of claim 9 wherein the integral assembly comprises up to 7 spaced containers.

16. The kit of claim 10 wherein the integral assembly comprises up to 16 spaced containers.

17. The kit of claim 11 wherein the integral assembly comprises up to 25 spaced containers.

18. The kit of claim 1 wherein the holder further comprises a kit information display element.

19. The kit of claim 18 wherein the holder further comprises a cover mated to the top surface and the cover comprises an attachment element configured to attach the kit information display element to the cover, wherein the kit information display element is a tablet or mobile device.

20. The kit of claim 19 wherein the cover comprises an inner surface and an outer surface, wherein the inner surface is positioned to face the top surface of the holder and the attachment element is affixed to the inner surface to attach the kit information display element to the inner surface of the cover, wherein the kit information display element is a tablet or mobile device.

21. The kit of claim 18 wherein the kit information display element comprises instructions for set-up of the kit, instructions for use of the kit, or combinations thereof.

22. The kit of claim 1 further comprising an identifier comprising non-volatile memory including kit set-up information, kit usage information, or combinations thereof.

23. The kit of claim 22 wherein the non-volatile memory comprises an RFID tag, a bar code, ICC, an EPROM, or EEPROM.

24. The kit of claim 22 wherein the identifier comprises a bar code.

25. The kit of claim 1 further comprising a fluid reservoir.

26. The kit of claim 25 wherein the fluid reservoir is adapted to receive a disposable fluid reservoir.

27. The kit of claim 1 further comprising a multi-well assay plate.

28. The kit of claim 27 wherein the holder further comprises a kit information display element.

29. The kit of claim 27 wherein the kit information display element comprises instructions for set-up of the kit, instructions for use of the kit, or combinations thereof.

30. The kit of claim 29 wherein the instructions comprise assay reagent preparation, multi-well plate preparation, or combinations thereof.

31. The kit of claim 27 further comprising an identifier comprising non-volatile memory including kit set-up information, kit usage information, or combinations thereof.

32. The kit of claim 31 wherein the kit set-up information comprises assay reagent preparation, multi-well plate preparation, or combinations thereof.

33. The kit of claim 1, wherein the spaced containers are arranged in the aligned series by a series of aligned tethers.

* * * * *